United States Patent [19]

Barth

[11] 4,452,796

[45] Jun. 5, 1984

[54] 6-AMINOALKYLPENICILLANIC ACID 1,1-DIOXIDES AS BETA-LACTAMASE INHIBITORS

[75] Inventor: Wayne E. Barth, East Lyme, Conn.

[73] Assignee: Pfizer Inc., New York, N.Y.

[21] Appl. No.: 434,371

[22] Filed: Oct. 21, 1982

Related U.S. Application Data

[63] Continuation-in-part of Ser. No. 388,324, Jun. 14, 1982, abandoned, which is a continuation-in-part of Ser. No. 338,797, Jan. 11, 1982, abandoned.

[51] Int. Cl.$^3$ .................. A61K 31/545; A61K 31/43; C07D 499/00; C07D 499/46
[52] U.S. Cl. ................................. 424/246; 260/239.1; 260/245.2 R; 424/269; 424/271
[58] Field of Search ................. 260/245.2 R, 239.1; 424/246, 271, 267

[56] References Cited

U.S. PATENT DOCUMENTS

| | | | |
|---|---|---|---|
| 3,487,079 | 12/1969 | Sheehan | 260/245.2 R X |
| 4,207,323 | 6/1980 | Beattie et al. | 424/270 |
| 4,234,579 | 3/1979 | Barth | 424/246 |
| 4,237,051 | 2/1980 | McCombie | 260/245.2 R |
| 4,244,951 | 1/1981 | Bigham | 424/250 |
| 4,260,598 | 4/1981 | Barth | 424/114 |
| 4,287,181 | 9/1981 | Kellogg | 424/271 X |
| 4,309,347 | 1/1982 | Bigham | 260/245.2 R |
| 4,342,768 | 8/1982 | Kellogg | 424/250 |
| 4,342,772 | 8/1982 | Godtfredsen et al. | 424/271 |

FOREIGN PATENT DOCUMENTS 2053220  2/1981  United Kingdom .

OTHER PUBLICATIONS

Sheehan et al., J. Org. Chem., 42, pp. 4045–4048, (1977).

*Primary Examiner*—Natalie Trousof
*Assistant Examiner*—Vera C. Clarke
*Attorney, Agent, or Firm*—Charles J. Knuth; Albert E. Frost; Robert K. Blackwood

[57] ABSTRACT

Beta-lactamase inhibitors which are 6-alpha- and 6-beta-(aminomethyl) and (1-aminoethyl)pencillanic acid 1,1-dioxides; pharmaceutically-acceptable salts thereof; conventional esters thereof which are hydrolyzable in vivo; bis-methanediol esters thereof; or mixed methanediol esters with said beta-lactamase inhibitors and sulbactam. Pharmaceutical compositions comprising said beta-lactamase inhibitors and a conventional beta-lactam antibiotic, used in the treatment of bacterial infections. Compounds useful as intermediates in the synthesis of said beta-lactamase inhibitors. Antibacterial mixed bis-methanediol esters of said aminoalkyl penicillanic acid 1,1-dioxides and ampicillin or amoxicillin, also used in the treatment of bacterial infections; and intermediates therefor.

55 Claims, No Drawings

6-AMINOALKYLPENICILLANIC ACID 1,1-DIOXIDES AS BETA-LACTAMASE INHIBITORS

CROSS REFERENCE TO RELATED APPLICATIONS

This application is a continuation-in-part of copending application Ser. No. 388,324, filed June 14, 1982, now abandoned which is a continuation-in-part of application Ser. No. 338,797, filed Jan. 11, 1982, and now abandoned. Copending application Ser. No. 388,323, also filed June 14, 1982, is also a continuation-in-part of the same application Ser. No. 338,797.

BACKGROUND OF THE INVENTION

The present invention relates to 6-alpha- and 6-beta-(aminomethyl and 1-aminoethyl)penicillanic acid 1,1-dioxides, pharmaceutically-acceptable salts thereof, conventional esters thereof which are hydrolyzable in vivo, bis-methanediol esters thereof; or mixed methanediol esters with said beta-lactamase inhibitors and sulbactam (penicillanic acid 1,1-dioxide), said methanediol esters also hydrolyzable in vivo. While some of these compounds possess antibacterial activity per se, their principal value is as beta-lactamase inhibitors. Thus they are useful in combination with conventional beta-lactam antibiotics (penicillins and cephalosporins) against microorganisms resistant or partially resistant to beta-lactam antibiotics through production of beta-lactamase enzymes. Also encompassed by the present invention are pharmaceutical compositions comprising a present beta-lactamase inhibiting compound and a known beta-lactam antibiotic; mixed bis-methanediol esters of the present beta-lactamase inhibiting compounds and either ampicillin or amoxicillin; pharmaceutical compositions of the latter mixed esters; methods of treating bacterial infections with either of the above pharmaceutical compositions; and compounds useful as intermediates in the preparation of these various compounds.

Related compounds, viz, penicillanic acid 1,1-dioxide and esters thereof readily hydrolyzable in vivo (Barth, U.S. Pat. No. 4,234,579); the bis-methanediol ester of sulbactam (Bigham, U.S. Pat. No. 4,309,347); various 6-beta-(hydroxymethyl)penicillanic acid 1,1-dioxides and esters thereof (Kellogg, U.S. Pat. No. 4,287,181); and 6-beta-(aminomethyl)penicillanic acid (McCombie, U.S. Pat. No. 4,237,051) have been previously described as beta-lactamase inhibitors useful in combination with beta-lactam antibiotics for the treatment of bacterial infections. Antibacterial bis-esters of methanediol with penicillins and penicillanic acid 1,1-dioxide (Bigham, U.S. Pat. No. 4,244,951; Godtfredsen et al., U.S. Pat. No. 4,342,772) have also been described.

U.K. patent application No. 2,053,220, published Feb. 4, 1981, broadly discloses beta-lactamase inhibiting compounds of the formula

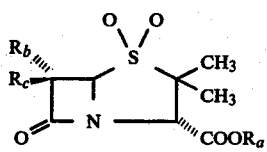

The definitions of $R_a$, $R_b$ and $R_c$ define literally an infinite number of compounds. These definitions, by appropriate selection of $R_a$, $R_b$ and $R_c$, may possibly define the simple 6-alpha and 6-beta-(aminoalkyl)penicillanic acid 1,1-dioxides of the present invention. No specific method for preparation of these compounds is present in the disclosure of this U.K. application, and there is no hint or suggestion that from among the infinity of compounds proposed, the present aminomethyl and 1-aminoethyl compounds are preferred compounds, possessing the particularly highly potent beta-lactamase inhibitory activity which we have determined for them.

SUMMARY OF THE INVENTION

The present invention relates to compounds of the formulae

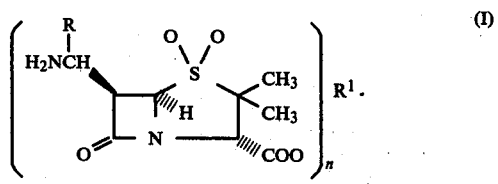

and

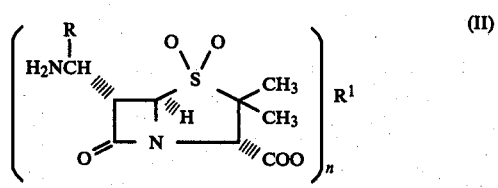

wherein
R is hydrogen or methyl; and
n is 1 and $R^1$ is hydrogen, a radical group forming an ester hydrolyzable under physiological conditions, or 1,1-dioxopenicillanoyloxymethyl; or
n is 2 and $R^1$ is —$CH_2$—;
the pharmaceutically-acceptable acid addition salts thereof; and
the pharmaceutically-acceptable cationic salts thereof when $R^1$ is hydrogen.

It will be understood by those skilled in the art that when R is methyl, each of the formulae (I) and (II) represent two different diastereoisomers (epimers). Depending on absolute stereochemistry, the side chains of these epimeric pairs are designated 1R-aminoethyl and 1S-aminoethyl. In each case one epimer has side chain configuration R and the other S. The same is true with respect to the formulae (III) and (IV), (V) and (VI), and (VII) and (VIII) below. These isomer pairs are generally separable by column chromatography at a variety of stages in the overall processes which are detailed below.

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid, having beta-lactamase activity. Preferred esters show no tendency to hydrogenolyze under the conditions preferably employed for their preparation (see below). The more preferred ester forming radicals are:

gamma-butyrolacton-4-yl,
—CHR²OCOR³, and
—CHR²OCOOR³, wherein $R^2$ is hydrogen or methyl and $R^3$ is ($C_1$-$C_6$)alkyl. The most preferred radicals are pivaloyloxymethyl and 1-ethoxycarbonyloxyethyl.

When n is 1 and $R^1$ is 1,1-dioxopenicillanoyloxymethyl,

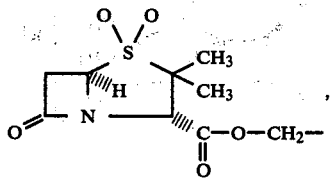

the compounds of the formulae (I) and (II) are diesters of methanediol. Such esters are also hydrolyzable under physiological conditions, yielding the parent acid of the formula (I) or (II), wherein n is 1 and $R^1$ is H, and penicillanic acid 1,1-dioxide. The latter compound also possesses beta-lactamase inhibitory activity. When n is 2 and $R^1$ is —$CH_2$—, the bis-ester is likewise hydrolyzed under physiological conditions, now producing two molecules of the parent acid from each molecule of the bis-ester.

Both the 6-beta-compounds (I) and the 6-alpha-compounds (II), regardless of side chain stereochemistry when R is methyl, are potent beta-lactamase inhibitors. For oral use, it is preferred that $R^1$ is other than hydrogen. When $R^1$ is a radical group forming an ester hydrolyzed in vivo, the preferred radicals are defined above. Because it is readily prepared in a highly pure, crystalline state (directly useful in mammals as a pharmaceutically-acceptable salt) pivaloyloxymethyl 6-alpha-(aminomethyl)penicillanate 1,1-dioxide p-toluenesulfonate salt is a particularly valuable compound in this series. Also readily prepared and of special value for oral use are the 6-alpha(aminomethyl)derivatives (II) wherein n is 1 and $R^1$ is 1,1-dioxopenicillanoyloxymethyl or n is 2 and $R^1$ is —$CH_2$—.

The compounds of the formulae (I) and (II) are useful as inhibitors of beta-lactamase enzymes. By this mechanism, these compounds enhance the activity of beta-lactam antibiotics (penicillins and cephalosporins), particularly against those microorganisms which are resistant or partially resistant to the beta-lactam antibiotic through the production of enzymes (beta-lactamases) which would otherwise destroy or partially destroy the beta-lactam antibiotic. In this manner, the spectrum of activity of the beta-lactam antibiotic is increased.

The beta-lactam antibiotics are one of the most well-known and widely-used class of antibacterial agents. These compounds are characterized by a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. While the present compounds are effective in enhancing the activity of beta-lactam antibiotics in general, their preferred use is found in their combination with a penicillin or cephalosporin of established clinical utility, viz., amoxicillin, ampicillin, azlocillin, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefonicid, cefmenoxime, cefodizime, cefoperazone, ceforanide, cefotaxime, cefoxitin, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, hetacillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin and ticarcillin, including the pharmaceutically-acceptable salts thereof. The names employed for these beta-lactams are generally USAN, i.e., U.S. Adopted Names. Preferred combinations are with ampicillin or an ampicillin derivative, with amoxicillin or an amoxicillin derivative or, most particularly, with cefoperazone.

Although the compounds of the present invention can be administered separately from the beta-lactam antibiotic, combination dosage forms are preferred. The pharmaceutical composition, whether for oral or parenteral use, comprises in a ratio of 1:3 to 3:1 by weight a beta-lactamase inhibitor of the formula (I) or (II) and a beta-lactam antibiotic, in total amounts sufficient to successfully treat a bacterial infection in a mammal in a single or, more usually, multiple doses.

Also encompassed by the present invention are antibacterial compounds having the stereochemical formulae

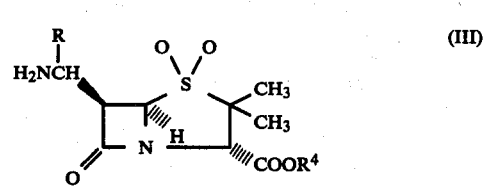

and

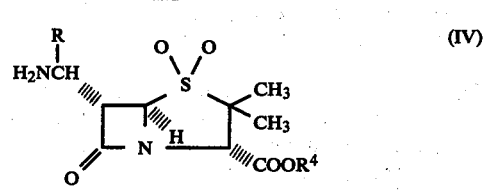

wherein
R is hydrogen or methyl; and
$R^4$ is

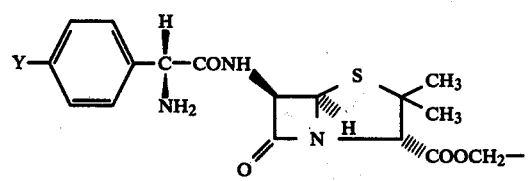

wherein Y is
hydrogen,
hydroxy, (C$_2$–C$_7$)-alkanoyloxy,
(C$_2$–C$_7$)-alkoxycarbonyloxy,
benzoyloxy, or
benzoyloxy monosubstituted with (C$_1$–C$_4$)-alkyl, (C$_1$–C$_4$)alkoxy or halo;
and the pharmaceutically-acceptable mono- and diacid addition salts thereof, the acids being as described above.

These bis-methanediol esters (III) and (IV) are effective as antibacterials through their in vivo hydrolysis to the corresponding beta-lactamase inhibitors of the formulae (I) and (II) wherein R$^1$ is hydrogen and to the corresponding ampicillin, amoxicillin or amoxicillin substituted on phenolic oxygen. It will be further noted that such phenolic esters are also generally hydrolyzed in vivo to produce amoxicillin. The bis-methanediol ester compounds are formulated into pharmaceutical compositions, suitable for either parenteral or oral administration in single or (more usually) multiple dosage for the treatment of bacterial infections in mammals.

Preferred compounds of the formulae (III) and (IV) have Y as hydrogen or hydroxy; most preferred compounds have Y as hydrogen.

Further encompassed by the present invention are intermediates of the stereochemical formulae

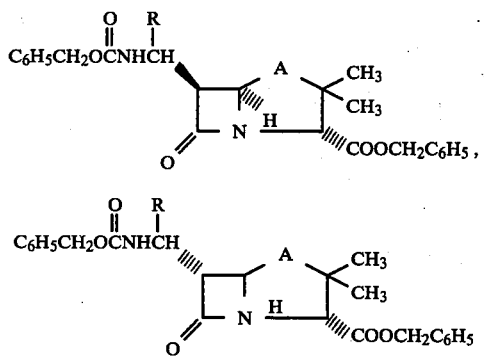

wherein A is

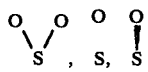

or S; and R is hydrogen or methyl;

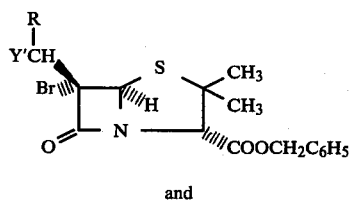

and

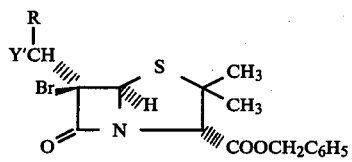

wherein Y' is
benzyloxycarbonylamino
amino
azido or
trifluoromethanesulfonyloxy; and
R is hydrogen or methyl.

DETAILED DESCRIPTION OF THE INVENTION

Those compounds of the present invention of the formulae (I) and (II) are generally prepared from benzyl 6,6-dibromopenicillanate or from benzyl 6-alpha-iodopenicillanate.

A preferred route, particularly for the 6-beta-(aminomethyl) series, involves as a first stage conversion of the dibromo compound to an epimeric mixture of mono-Grignard reagents. This is conveniently done by an exchange reaction using essentially one molar equivalent of methyl magnesium bromide in an ether solvent (ether, tetrahydrofuran, dimethoxyethane) at low temperature (−50° to −100° C.), conveniently at −78° C., the temperature of an acetone-dry ice bath. After a brief reaction time (5–30 minutes) at such reduced temperature, the mono-Grignard reagents are contacted with essentially 0.5 molar equivalents of benzyloxycarboxamidomethyl acetate (usually diluted with the same ether solvent and added to the cold Grignard reagent at such a rate that the low temperature of the reaction is maintained). Reaction time is not critical; 0.5 to 2 hours at −50° to −100° C. is usually sufficient to achieve complete reaction. Mixed epimers of the above formulae (VII) and (VIII) wherein Y' is benzyloxycarbonylamino are readily recovered by acetic acid quench, concentration and chromatography. The mixture of epimers can be used directly in the next step, or if desired, separated by further column chromatography on silica gel.

The next step of the sequence is reductive removal of the bromine atom, conveniently accomplished by the action of excess tri-n-butyltin hydride, optionally in the presence of small amounts (less than 0.1 molar equivalents) of a free radical initiator such as 2,2'-azobisisobutyronitrile (AIBN). Here and hereinafter, "reaction-inert solvent" is defined as a solvent which does not react with starting materials, reagents, intermediates or products in a manner which significantly reduces the yield of the desired product. Well-suited in the present case are hydrocarbon solvents such as benzene or toluene. Temperature should be elevated (60°–100° C.), such that reaction occurs in a reasonable time, but not so high as to cause undue thermal degradation. When this step is carried out on the mixed epimer precursors, the 6-beta-epimer (V), wherein A is S, is generally recovered by crystallization; if desired the 6-alpha-epimer (VI, A=S) is recovered from the mother liquors by evaporation and chromatography.

A second preferred route, particularly for the 6-alpha(aminomethyl) series, is to react a cold ether solution of the Grignard reagent from benzyl 6-alphaiodopenicillanate with a benzyloxycarboxamidomethyl acetate under conditions described above. The resulting mixture of compounds (V) and (VI), wherein A is S, can be separated by column chromatography, but preferably are oxidized to 1,1-dioxides and then subjected to C-6 epimerization conditions to yield the clean alpha-epimer (VI, A=SO$_2$) as detailed below.

To form the 1-alpha and 1-beta oxides of the formulae (V) and (VI), wherein A is S∥O or S→O, the above sulfides of the formulae (V) and (VI), wherein A is S, are oxidized with substantially 1 molar equivalent of a peracid, conveniently m-chloroperbenzoic acid, in a reaction-inert solvent such as ethyl acetate at 0°–50° C.

When benzyl 6-beta-(benzyloxycarbonylaminomethyl)-penicillanate (V, R=H, A=S) is oxidized, the resulting alpha-oxide (V, R=H, A=S→O) is isolated by crystallization, while the beta-oxide (V, R=H, A=S→O) is isolated from mother liquors by evaporation. If desired, other standard sulfoxide forming reagents can be used.

If desired, benzyl 6-beta-(benzyloxycarbonylaminomethyl)penicillanate 1-beta-oxide (V, A=S→O) is rearranged to the corresponding 6-alpha epimer (VI, A=S→O) by contacting the former with an equivalent of 1,5-diazabicyclo[4.3.0]non-5-ene (DBN) at 0°–50° C., conveniently at 25° where reaction is complete in a very short time (3–15 minutes). In like manner a 6-beta dioxide (V, A=SO$_2$) is converted to its 6-alpha epimer (VI, A=SO$_2$).

Oxidation of the sulfides (V) and (VI), wherein A is S, or further oxidation of the above sulfoxides, with excess peracid (but otherwise under conditions as generally described above for mono-oxide formation) yields the corresponding sulfones (1,1-dioxides) of the formulae (V) and (VI), wherein A is SO$_2$. If desired, other sulfone forming reagents such as KMnO$_4$ can be used.

Hydrogenolyis of the resulting benzyl 6-(alpha or beta)(benzyloxycarbonylaminoalkyl)penicillanate 1,1-dioxides, (V and VI, A=SO$_2$) produces the corresponding 6-(alpha or beta)(aminomethyl or 1-aminoethyl)penicillanic acids (I and II, R$^1$=H). Hydrogenolysis is carried out by methods well-known in the penicillin art. The substrate, in a reaction-inert solvent, is contacted with hydrogen in the presence of a noble metal catalyst, such as palladium, platinum or rhodium, optionally in the form of its oxide or a salt, or on a carrier such as carbon, an alkaline earth carbonate or alumina. Temperature is not critical (e.g. 0°–50° C.), but is preferably 25° C. or lower in order to minimize thermal degradation. Pressure can be varied over a wide range (subatmospheric to 100 atmospheres), but as a matter of convenience will generally be in the range of 1 to 7 atmospheres. The reaction inert solvent is preferably relatively low boiling so as to be readily removed by concentration in vacuo. Aqueous tetrahydrofuran is a solvent particularly well-suited for the present purpose. The preferred catalyst is palladium, supported on carbon.

To prepare an in vivo hydrolyzable ester [i.e., a compound of the formulae (I) or (II), wherein R$^1$ is a radical group forming an ester which is hydrolyzable under physiological conditions], the amino group of the 6-(aminoalkyl)penicillanic acid 1,1-dioxide is first protected with a benzyloxycarbonyl group, using methods well-known in the art. For example, benzyl chloroformate is added slowly to the amine in a reaction-inert solvent such as aqueous acetone or aqueous tetrahydrofuran while maintaining pH 8.0 at a temperature of 0°–35° C., preferably 0°–20° C. In this manner, compounds of the formulae (IX) and (X), wherein R$^1$ is H, are formed. Alternatively, such compounds are formed by the partial hydrogenolysis of compounds of the formula (V) and (VI) wherein A is SO$_2$. Except to limit hydrogen uptake, conditions as described above are used.

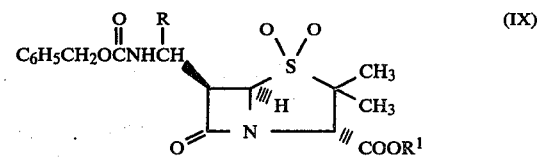

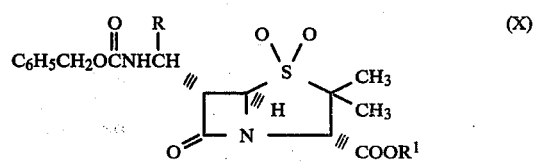

The latter intermediates are then converted to the desired esters of the formulae (IX) and (X), wherein R$^1$ now represents an in vivo hydrolyzable ester, according to known methods, readily identified by those skilled in the penicillin art (see for example U.S. Pat. Nos. 4,234,579 and 4,287,181; and European patent publication No. 40,494). Preferred ester values of R$^1$ have been defined above; preferred methods for the preparation of such esters are detailed in specific examples below and in European patent publication No. 40,494.

The protected esters (IX) and (X) are converted to the desired esters of the formula (I) or (II), retaining R$^1$ as the ester functionality by hydrogenolysis, preferably in the presence of a weakly acidic buffer comprising equimolar quantities of a weakly basic amine, such as pyridine, and a strong acid such as a mineral acid (e.g. HCl, HNO$_3$, H$_2$SO$_4$) or preferably a sulfonic acid (such as methanesulfonic acid, benzenesulfonic acid or p-toluenesulfonic acid), otherwise according to methods described above, taking care to minimize exposure to conditions (e.g. water, lower alcohols, high acidity or basicity) which will cause hydrolysis of the sensitive ester or beta-lactam groups. It is preferred to isolate the ester directly from the reaction mixture in the form of the acid addition salt where the acid is the one used in the buffer. A particularly preferred buffer is pyridinium p-toluenesulfonate in which case the product is usually isolated as its p-toluenesulfonate salt.

The above-defined pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. As noted above, the salt is alternatively isolated directly from a reaction mixture, i.e., without isolation of the free amine, otherwise using similar techniques of concentration and/or addition of a non-solvent.

The above-defined pharmaceutically-acceptable cationic salts of those compounds of the present invention having a free carboxylic acid group are also readily prepared by standard methods. For example, an equivalent of the corresponding cationic hydroxide, carbonate or bicarbonate or of an amine is combined with the carboxylic acid in an organic or aqueous solvent, preferably at reduced temperature (e.g. 0°–5° C.), with vigorous agitation and slow addition of the base. The salt is isolated by concentration and/or the addition of a non-solvent. In some cases, the salt is isolated directly from a reaction mixture, without isolation of the free acid form.

The bis-methanediol esters (III) and (IV), as well as those of the formulae (I) and (II) wherein n is 1 and $R^1$ is 1,1-dioxopenicillanoyloxymethyl or wherein n is 2 and $R^1$ is —$CH_2$—, are also prepared from the amino protected penicillanic acids acids (IX) and (X), wherein $R^1$ is H. In one alternative, the latter compounds are first converted to the corresponding chloromethyl esters. The preferred method is to convert the acid to its tetrabutylammonium salt, which is then reacted with excess chloromethyl bromide or iodide at 0°–50° C., preferably at 25° or less.

Although a chloromethyl ester can be used directly in the next step, it is preferred to first convert the chloromethyl ester to the corresponding iodomethyl ester. Contact of the chloromethyl ester with sodium iodide in acetone at 0°–50° until reaction is substantially complete represents conditions particularly well-suited to this purpose.

The iodomethylester is then reacted, in a reaction inert solvent at 0°–50° C., with a salt of penicillanic acid 1,1-dioxide; a salt of the same amino protected penicillanic acid (IX) or (X) wherein $R^1$ is H; a salt of azidocillin [6-(D-2-phenyl-2-azidoacetamido)penicillanic acid]; or a salt of an ampicillin or amoxicillin derivative of the formula

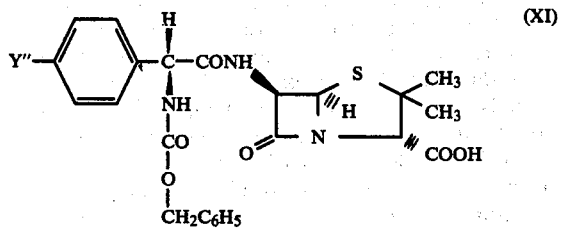

wherein Y'' is H, benzyloxycarbonyloxy, ($C_2$–$C_7$)alkoxycarbonyloxy, benzoyloxy, or benzoyloxy mono-substituted with ($C_1$–$C_4$)alkyl, ($C_1$–$C_4$)alkoxy or halo (F, Cl or Br). The preferred salt is the tetrabutylammonium salt, since it reacts very rapidly with the iodomethyl ester, minimizing degradation.

In a second alternative, the bis-methanediol esters (III) and (IV), as well as the esters of the formula (I) or (II) where n is 1 and $R^1$ is 1,1-dioxopenicillanoyloxymethyl are prepared by reacting the above salt of an amino protected penicillanic acid (IX) or (X), wherein $R^1$ is H, with a halomethyl ester (preferably an iodomethyl ester) of penicillanic acid 1,1-dioxide, of azidocillin, or of an ampicillin or amoxicillin derivative of the formula (XI) above.

In either alternative, the resulting protected methanediol diester is then converted to the desired end product of the formula (I), (II) [where n is 1 and $R^1$ is 1,1-dioxopenicillanoyloxymethyl or n is 2 and $R^1$ is —$CH_2$—], (III) or (IV) by hydrogenolysis, using methods detailed above; again minimizing exposure to conditions which cleave the sensitive methanediol ester bonds. The pharmaceutically-acceptable mono- or di-acid addition salts of these methanediol diesters are prepared using one or two equivalents of the acid, as appropriate, according to methods described above.

Another preferred route to the intermediates of the formulae (VII) and (VIII) wherein Y' is benzyloxycarbonylamino, particularly when R is methyl, is to prepare them from the corresponding known benzyl 6-alpha-(hydroxymethyl or 1-hydroxyethyl)-6-beta-bromopenicillanate and benzyl 6-beta-(hydroxymethyl or 1-hydroxyethyl)-6-alpha-bromopenicillanate (also prepared from benzyl 6,6-dibromopenicillanate).

In the first stage, the above hydroxymethyl or 1-hydroxyethyl compounds are converted to the corresponding trifluoromethanesulfonate esters (VII and VIII, Y'=trifluoromethanesulfonyloxy). This reaction is conveniently carried out at room temperature using trifluoromethanesulfonic anhydride as reagent, in a reaction inert solvent such as methylene chloride in the presence of at least one equivalent of a tert-amine such as pyridine or diisopropylethylamine.

In the second stage the sulfonate group is displaced by azide, forming the azidomethyl compounds of the formulae (VII) and (VIII), wherein Y' is azido. An excellent reagent for this purpose is tetramethylguanidinium azide in moderate excess. The reaction is carried out at 0°–25° C., preferably about 10° C., in a reaction-inert solvent such as chloroform or methylene chloride.

In the third stage the azido group is reduced to an amino group, yielding compounds of the formulae (VII) and (VIII) wherein Y' is amino. A convenient reagent for this purpose is hydrogen sulfide, in the presence of a tertiary amine such as triethylamine in a reaction-inert solvent such as chloroform. Gaseous hydrogen sulfide is bubbled through the reaction mixture at 0°–50° C. until reduction is substantially complete (usually about 3–4 hours at 25°).

Finally, the amino group is protected with a benzyloxycarbonyl group, using conditions standard in the art. For example benzyl chloroformate as reagent in the presence of a tertiary amine such as pyridine or N,N-diisopropylethyl amine, in a reaction-inert solvent such as methylene chloride at 0°–50° C., preferably at reduced temperature (0°–10° C.). The resulting compounds of the formulae (VII) and (VIII) wherein Y' is benzyloxycarbonylamino are then further processed according to methods detailed above.

As indicated above, some of the compounds of the formulae (I) and (II), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Those compounds of the formulae (I) and (II) having said in vitro antibacterial activity are thus useful as industrial antimicrobials, for example in water treatment, slime control, paint preservation and wood preservation, as well as for topical application as a disinfectant. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formulae (I) and (II) are of more particular value as potent inhibitors of microbial beta-lactamases. By this mechanism they increase the antibacterial effectiveness of beta-lactam antibiotics (penicillins and cephalosporins) against many microorganisms, particularly those which produce a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) or (II) (having $R^1$ as hydrogen) alone, are determined. These MIC's are then compared with the MIC values obtained with a combination of the given antibiotic and the compound of the formula (I) or (II), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) enhance the antibacterial effectiveness of beta-lactam antibiotics in vivo. That is, they lower the amount of the antibiotic which is neeced to protect mice against an otherwise lethal inoculum of certain beta-lactamase producing bacteria. In determining such activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound in combination with the antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection). Compounds of the formulae (III) and (IV) are tested for in vivo activity in like manner, except that they are generally dosed alone, not in combination with other beta-lactam antibiotics.

In determining whether a particular strain of bacteria is sensitive to a particular compound of the formula (III) or (IV) it is not necessary to carry out an in vivo test. Instead, the MIC of a 1:1 mixture of a compound of the formula (I) or (II), wherein $R^1$ is hydrogen, and ampicillin or amoxicillin, as appropriate, are measured according to methods described above.

The ability of the compounds of formulae (I) and (II) to enhance the effectiveness of a beta-lactam antibiotic against beta-lactamase producing bacteria makes them valuable for coadministration with beta-lactam antibiotics in the treatment of bacterial infections in mammals, particularly man. In the treatment of a bacterial infection, the compound of the formula (I) or (II) can be comingled with the beta-lactam antibiotic, and the two agents thereby administered simultaneously. Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) to enhance the effectiveness of beta-lactam antibiotic, a mixture of (I) or (II) with the beta-lactam antibiotic is administered preferably in formulation with standard pharmaceutical carriers or diluents. A pharmaceutical composition comprising a pharmaceutically acceptable carrier, a beta-lactam antibiotic and a compound of formula (I) or (II) will normally contain from about 5 to about 80 percent of the pharmaceutically acceptable carrier by weight.

When using the compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula (I) or (II) and the beta-lactam antibiotic will normally be in the range from about 1:3 to 3:1 by weight. Additionally, when using the compounds of formula (I) or (II) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e. comingled) with a beta-lactam antibiotic which is effective only on parenteral administration, a combination formulation suitable for parenteral use will be required. When a compound of formula (I) or (II) is to be used simultaneously (comingled) with a beta-lactam antibiotic which is effective orally or parenterally, combinations suitable for either oral or parenteral administration can be prepared. Additionally, it is possible to administer preparations of the compounds of formula (I) orally, while at the same time administering a further beta-lactam antibiotic parenterally; and it is also possible to administer preparations of the compounds of formula (I) parenterally, while at the same time administering the further beta-lactam antibiotic orally.

It is the capacity of compounds of the formula (III) or (IV) to hydrolyze and provide both the compounds of the formula (I) or (II), wherein $R^1$ is hydrogen, and ampicillin or amoxicillin, which enhances the activity and broadens the antibacterial spectrum of these compounds relative to the use of an equivalent amount of ampicillin or amoxicillin alone, particularly by the oral route.

When using the present antibacterial compounds of the formula (III) or (IV) for control of bacterial infections in a mammal, particularly man, the compound is administered alone, or mixed with pharmaceutically acceptable carriers or diluents. Said carrier or diluent is chosen on the basis of the intended mode of administration. For oral administration, tablets, capsules, lozenges, troches, powders, syrups, elixirs, aqueous solutions and suspensions, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

When using compounds of the formula (III) or (IV) to control bacterial infections, the daily dosage will be similar to that of other clinically used beta-lactam antibiotics. Although the prescribing physician will ultimately decide the dosage to be used in a human subject, the compounds of formula (III) or (IV) will normally be used orally at dosages in the range from about 20 to about 100 mg per kilogram of body weight per day, and parenterally at dosages from about 10 to about 100 mg per kilogram of body weight per day, usually in divided doses. In some instances, the prescribing physician will determine that dosages outside these limits are needed.

The present invention is illustrated by the following examples. However, it should be understood that the invention is not limited to the specific details of these examples. Unless otherwise specified, proton nuclear magnetic resonance spectra are 60 MHz.

EXAMPLE 1

Benzyl 6-alpha-bromo-6-beta-(benzyloxycarbonylaminomethyl)penicillanate and 6-beta-bromo-6-alpha-(benzyloxycarbonylaminomethyl)penicillanate To a solution of benzyl 6,6-dibromopenicillanate (108.73 g, 0.242 mole) in 600 ml dry tetrahydrofuran (THF), cooled to −78° C., was added an ether solution of methyl magnesium bromide (83.5 ml of 2.9 M). After stirring for 15 minutes at −78° a solution of benzyloxycarboxamidomethyl acetate (27 g, 0.121 mole) in 200 ml dry THF was added over 10 minutes. After stirring for an hour at −78° the reaction was quenched by the addition of 14.52 ml of acetic acid. The mixture was warmed to room temperature and volatiles removed in vacuo at less than 35° C. Ethyl acetate was added to dissolve the residue, and the solution washed with water (100 ml), aqueous NaHCO$_3$ (100 ml), and 2×100 ml water, then dried over Na$_2$SO$_4$ and concentrated in vacuo to 113 g of oily product. The oil was column chromatographed on 1.2 kg silica gel, eluting first with 6 liters of 1:1 hexane:chloroform and then with chloroform. The first 6 liters of eluate was discarded. Further eluate was collected in 25 ml fractions. Fraction numbers 181–190 were concentrated. The pnmr spectrum of the residue in CDCl$_3$ revealed benzyl 6-alpha-bromo-6-beta-(benzyloxycarbonylaminomethyl)penicillanate: delta/TMS 1.37 (3H, s), 1.57 (3H, s), 3.86 (2H, d, J=6 Hz), 4.42 (1H, s), 5.06 (2H, s), 5.12 (2H, s), 5.52 (1H, s), 7.25 (10H, s). Fraction numbers 201–249 were concentrated and the pnmr spectrum of this residue in CDCl$_3$ revealed benzyl 6-beta-bromo-6-alpha-(benzyloxycarbonylaminomethyl)penicillanate: delta/TMS 1.36 (3H, s), 1.60 (3H, s), 390 (2H, d, J=6.2 Hz), 4.47 (1H, s), 5.07 (2H, s), 5.14 (2H, s), 5.40 (1H, t, J=6.2), 5.47 (1H, s), 7.28 (5H, s), 7.30 (5H, s). The product from fraction numbers 171–240 was combined and concentrated to 22 g of foam and used in the experiment of Example 2.

EXAMPLE 2

Benzyl 6-beta-(Benzyloxycarbonylaminomethyl)penicillanate

To a solution of title products (epimeric mixture) of the preceding Example (22 g, 0.0413 mole) in 100 ml benzene was added tri-n-butyltin hydride (32.7 ml, 0.124 mole). The mixture was refluxed under N$_2$ for 2 hours, concentrated in vacuo to an oil and the oil triturated 4×100 ml hexane. The residual viscous oil was taken up in 70 ml of ether, from which title product crystallized over 1 hour [8.1 g in two crops] pnmr/CDCl$_3$/delta/TMS: 1.37 (3H, s), 1.57 (3H, s), 3.58 (3H, m), 4.34 (1H, s), 5.04 (2H, s), 5.12 (2H, s), 5.33 (1H, d, J=4 Hz), 7.32 (10H, s).

Benzyl 6-alpha-(benzyloxycarbonylaminomethyl)penicillanate is recovered by concentration of mother liquors and chromatography (see Example 33).

EXAMPLE 3

Benzyl 6-beta-(Benzyloxycarbonylaminomethyl)penicillanate 1-alpha-Oxide and

Benzyl 6-beta-(Benzyloxycarbonylaminomethyl)penicillanate 1-beta-Oxide

To a solution of title product of the preceding Example (4.54 g, 0.01 mole) in 70 ml of ethyl acetate was added m-chloroperbenzoic acid (2.02 g, 0.01 mole) in 30 ml ethyl acetate. The mixture was stirred 30 minutes at room temperature, washed 1×50 ml saturated NaHCO$_3$ and 2×50 ml H$_2$O, dried over Na$_2$SO$_4$ and concentrated in vacuo to a viscous oil. The oil was dissolved in 50 ml of ether and 10 ml CHCl$_3$ and crystallization of title alpha-oxide induced by scratching [2.2 g, mp 123°–124° C., pnmr/CDCl$_3$/delta/TMS 1.22 (3H, s), 1.51 (3H, s), 3.7 (3H, m), 4.34 (1H, s), 4.63 (1H, d, J=4 Hz), 5.13 (2H, s), 5.22 (2H, s), 5.50 (1H, m), 7.34 (5H, s), 7.40 (5H, s)]. Concentration of mother liquor to dryness in vacuo gave the title beta-oxide as a viscous oil [2.5 g; pnmr/CDCl$_3$/delta/TMS 1.05 (3H, s), 1.60 (3H, s), 3.8 (3H, m), 4.63 (1H, s), 4.73 (1H, d, J=4 Hz), 5.13 (2H, s), 5.23 (2H, q), 5.70 (1H, m), 7.35 (5H, s), 7.39 (5H, s)].

EXAMPLE 4

Benzyl 6-alpha-(Benzyloxycarbonylaminomethyl)penicillanate 1-beta-Oxide

To title beta-oxide of the preceding Example (2.3 g, 4.9 mmoles) in 100 ml $CHCl_3$ was added 1,5-diazabicyclo[4.3.0]non-5-ene (DBN, 0.607 g, 4.9 mmoles). The mixture was stirred at room temperature for 15 minutes, diluted with 50 ml 1 N HCl, and the layers separated. The organic layer was washed 2×50 ml $H_2O$, dried over $Na_2SO_4$ and concentrated in vacuo to an oil (2.3 g). The oil was column chromatographed on 100 g silica gel, eluting with 4:1 $CHCl_3$:ethyl acetate in 20 ml fractions. Fractions 41–70 were combined and concentrated in vacuo to yield title product as a viscous oil [0.9 g; pnmr/$CDCl_3$/TMS 1.03 (3H, s), 1.60 (3H, s), 3.67 (3H, m), 4.46 (1H, s), 4.88 (1H, m) 5.08 (2H, s), 5.17 (2H, q), 5.39 (1H, m), 7.32 (5H, s), 7.37 (5H, s)].

EXAMPLE 5

Benzyl 6-beta-(Benzyloxycarbonylaminomethyl)penicillanate 1,1-Dioxide

To a solution of title product of Example 2 (8.0 g, 0.0176 mole) in 200 ml ethyl acetate cooled to 0°–5° C. was added m-chloroperbenzoic acid (10.68 g, 0.0528 mole). The mixture was warmed to room temperature, stirred for 6 hours, recooled to 0°–5° C. and diluted with 50 ml of saturated $NaHSO_3$. The organic layer was separated, washed 2×50 ml saturated $NaHCO_3$ and 2×50 ml $H_2O$, dried over $Na_2SO_4$ and concentrated in vacuo to a viscous oil (8.6 g). The oil was chromatographed on 250 g silica gel, eluting with 19:1 $CHCl_3$:ethyl acetate in 25 ml fractions. Fractions 44–150 were combined and concentrated in vacuo to yield title product as a white gummy foam [7.6 g; pnmr/$CDCl_3$/delta/TMS 1.25 (3H, s), 1.49 (3H, s), 3.98 (3H, m), 4.45 (1H, s), 4.59 (1H, d, J=4 Hz), 5.09 (2H, s), 5.19 (2H, q), 5.36 (1H, br), 7.36 (10H, s)].

EXAMPLE 6

Benzyl 6-alpha-(Benzyloxycarbonylaminomethyl)penicillanate 1,1-Dioxide

By the procedure of Example 4, the title 1,1-dioxide of the preceding Example (3.3 g, 6.79 mmoles) was converted to present title product (3.1 g crude), and purified by column chromatography on 150 g silica gel, eluting with 1:9 ethyl acetate:$CHCl_3$ in 20 ml fractions. Fractions 26–37 were combined and concentrated in vacuo to yield purified title product, as a viscous oil which crystallized on standing [1.9 g; mp 112°–113° C.; pnmr/$CDCl_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s)].

Present title product was also obtained by the further oxidation of the title product of Example 4 with excess m-chloroperbenzoic acid according to the method of Example 5.

EXAMPLE 7

6-beta-(Aminomethyl)penicillanic Acid 1,1-Dioxide

Title product of Example 5 (1.9 g), THF (40 ml), $H_2O$ (40 ml) and 10% Pd/C (1.9 g) were combined and hydrogenated at 50 psig for 1 hour. Catalyst was recovered by filtration and THF removed from the filtrate in vacuo. The aqueous layer was washed with 30 ml ethyl acetate, freeze dried to a white powder and a first crystalline crop (0.26 g) obtained by trituration of the powder with 5 ml water. A second crop (0.14 g) crystallized on addition of 10 ml of acetone to the mother liquor and a third crop (0.35 g) by evaporating the second mother liquor to 2 ml and adding 50 ml of acetone. Total yield of title product was 0.75 g [pnmr/250 MHz/$D_2O$/delta/DSS 1.47 (3H, s), 1.59 (3H, s), 3.74 (2H, m), 4.36 (1H, td, J=4, 5.5 Hz), 4.45 (1H, s), 5.17 (1H, d, J=4 Hz)].

To obtain the potassium salt, title product (1.0 g) is dissolved in 30 ml of water and cooled in an ice water bath, one equivalent of 1 N KOH is added dropwise to the well-stirred solution, and the resulting solution freeze dried.

EXAMPLE 8

6-alpha-(Aminomethyl)penicillanic Acid 1,1-Dioxide

By the method of the preceding Example, title product of Example 6 (1.7 g) was converted to present title product, except that crystalline product was obtained directly by concentration in vacuo following the ethyl acetate extraction [0.7 g; pnmr/250 MHz/$D_2O$/DSS 1.44 (3H, s), 1.59 (3H, s), 3.63 (2H, d, J=5.5 Hz) 4.07 (1H, td, J=2, 5.5 Hz) 4.31 (1H, s), 5.06 (1H, d, J=2)].

To obtain the hydrochloride salt, product (0.7 g) is dissolved in water (30 ml), an equivalent of dilute hydrochloric acid is added dropwise, and the resulting solution freeze dried.

To obtain the sodium salt, product (0.7 g) is dissolved in water (30 ml). At 0°–5° C., one equivalent of dilute sodium hydroxide is added with vigorous stirring and the solution freeze dried.

EXAMPLE 9

Benzyl 6-beta-Bromo-6-alpha-trifluoromethanesulfonyloxymethylpenicillanate

To a solution of trifluoromethanesulfonic anhydride (3.15 ml) in methylene chloride (20 ml) at room temperature was added a solution of benzyl 6-beta-bromo-6-alpha-(hydroxymethyl)penicillanate (6.232 g, 15.6 mmoles) and pyridine (1.89 ml) in methylene chloride (20 ml) and the mixture stirred and cooled in an ice bath for 45 minutes. The methylene chloride was evaporated under reduced pressure and the residue partitioned between ethyl acetate and water. The ethyl acetate phase was separated and the aqueous phase extracted with additional ethyl acetate. The combined ethyl acetate solutions were washed first with sodium bicarbonate solution at pH 8.3 and then with brine. After drying over anhydrous sodium sulfate, the solution was evaporated under reduced pressure to give title product as an orange solid [8.296 g; pnmr/$CDCl_3$/delta/TMS 1.41 (s, 3H), 1.63 (s, 3H), 4.51 (s, 1H), 4.87 (s, 2H), 5.14 (s, 2H), 5.44 (s, 1H), 7.30 (s, 5H)].

EXAMPLE 10

Benzyl 6-alpha-Azidomethyl-6-beta-bromopenicillanate

Tetramethylguanidinium azide (2.96 g, 18.7 mmoles) was added to a solution of benzyl 6-beta-bromo-6-alpha-trifluoromethylsulfonyloxymethylpenicillanate (8.296 g, 15.6 mmoles) in chloroform (50 ml) at 10° C. The reaction mixture was stirred for one hour and then reduced to one third volume and filtered through a pad of silica gel. The pad was eluted with 10% ethyl acetate/chloroform (100 ml) and the eluate evaporated to give an amber oil [6.744 g; pnmr/CDCl$_3$/delta/TMS 1.38 (s, 3H), 1.61 (s, 3H), 3.96 (s, 2H), 4.53 (s, 1H), 5.17 (s, 2H), 5.40 (s, 1H), 7.34 (s, 5H)].

EXAMPLE 11

Benzyl 6-alpha-Bromo-6-beta-trifluoromethanesulfonyloxymethylpenicillanate

Following the procedure of Example 9, benzyl 6-alpha-bromo-6-beta-hydroxymethylpenicillanate (0.548 g, 1.4 mmoles) in methylene chloride (4 ml) containing pyridine (0.17 ml) was reacted with a solution of trifluoromethanesulfonic anyhdride (0.42 ml) in methylene chloride (3 ml) to give title product as an amber oil [641 mg; pnmr/CDCl$_3$/delta/TMS 1.43 (s, 3H), 1.62 (s, 3H), 4.52 (s, 1H), 4.88 (g, 2H), 5.19 (s, 2H), 5.62 (s, 1H), 7.35 (s, 5H)].

EXAMPLE 12

Benzyl 6-alpha-Bromo-6-beta-azidomethylpenicillanate

To a solution of benzyl 6-alpha-bromo-6-beta-trifluoromethanesulfonyloxymethylpenicillanate (641 mg, 1.2 mmoles) in chloroform (10 ml) was added tetramethylguanadinium azide (229 mg, 1.2 mmoles) at 10° C. The reaction mixture was stirred for one hour and then evaporated under reduced pressure. The oily residue was filtered through a pad of silica gel and eluted therefrom with 10% ethyl acetate/chloroform. Evaporation of the eluate gave title product as an amber oil [420 mg; pnmr/CDCl$_3$/delta/TMS 1.43 (s, 3H), 1.61 (s, 3H), 3.91 (s, 2H), 4.48 (s, 1H), 5.15 (s, 2H), 5.57 (s, 1H), 7.37 (s, 5H)].

EXAMPLE 13

Benzyl 6-alpha-(Aminomethyl)-6-beta-bromopenicillanate

Hydrogen sulfide was bubbled into a rapidly stirred solution of benzyl 6-alpha-azidomethyl-6-beta-bromopenicillanate (541 mg, 1.3 mmoles) and triethylamine (0.71 ml, 4 equivalents) in chloroform (10 ml) for one hour. The reaction mixture was then evaporated in vacuo to a red oil. NMR data showed the residue to comprise the desired product contaminated with triethylamine [pnmr/CDCl$_3$/delta/TMS 1.39 (s, 3H), 1.64 (s, 3H), 3.35 (s, 2H), 4.51 (s, 1H), 5.16 (s, 2H), 5.35 (s, 1H), 7.33 (s, 5H)].

By the same method, title product of Example 12 is converted to benzyl 6-beta-(aminomethyl)-6-alpha-bromopenicillanate.

EXAMPLE 14

Benzyl 6-beta-Bromo-6-alpha-benzyloxycarbonylaminomethyl)penicillanate

A solution of pyridine (0.14 ml) and benzyl 6-alpha-aminomethyl-6-beta-bromopenicillanate (239 mg, 0.6 mmoles) in methylene chloride (5 ml) was added via a syringe over a 5 minute period to a solution of benzylchloroformate in methylene chloride (5 ml) and the reaction mixture stirred in an ice bath under a nitrogen atmosphere for 75 minutes. The reaction mixture was evaporated in vacuo and the residue taken up in ethyl acetate/water. The pH was adjusted to 2.9 with dilute hydrochloric acid, the ethyl acetate phase separated and extracted with dilute sodium bicarbonate solution (pH 8.1), washed with brine and dried over anhydrous sodium sulfate. Evaporation under reduced pressure gave 312 mg which was taken up in chloroform and chromatographed on silica gel (15 g, 14×20 cm column) and eluted therefrom with 5% ethyl acetate/chloroform. Reactions of 4 ml each were collected. Fractions 14–27 were combined and evaporated under reduced pressure to give title product [168 mg, pnmr/CDCl$_3$/delta/TMS consistent with title product and identical with that of the same compound prepared in Example 1].

By the same method the beta-(aminomethyl) compound of the preceding Example is converted to benzyl 6-alpha-bromo-6-beta-(benzyloxycarbonylaminomethyl)penicillanate.

EXAMPLE 15

Benzyl 6-beta-(Benzyloxycarbonylaminomethyl)penicillanate

A solution of tri(n-butyl)tin hydride (0.25 ml) and benzyl 6-beta-bromo-6-alpha-(benzyloxycarbonylaminomethyl)penicillanate (168 mg, 0.31 mmoles) in benzene (4 ml) was refluxed for 2 hours. The benzene was then evaporated in vacuo and the residue triturated with hexane (3×2 ml). The remaining residue was then taken up in ethyl acetate/water, the ethyl acetate phase separated, washed with brine and dried over anhydrous sodium sulfate. Evaporation in vacuo gave 101 mg of an oil which was chromatographed on silica gel (4 g, 1×11 cm column), set up with chloroform and eluted with 5% ethyl acetate/chloroform. Fractions of 4 ml volume were collected. Fractions 3–5 were combined and evaporated to give title product (66 mg; identified by pnmr as identical with the product of Example 2).

EXAMPLE 16

6-alpha-(Benzyloxycarbonylaminomethyl)penicillanic Acid 1,1-Dioxide

Method A

Title product of Example 6 (11.2 g) in THF (70 ml) and H$_2$O (50 ml) in the presence of 6 g 10% Pd/C was partially hydrogenated at 50 psig for 30 minutes. Catalyst was removed by filtration over a pad of diatomaceous earth, THF was distilled from the filtrate in vacuo, and the aqueous residue was extracted with 100 ml ethyl acetate. The organic layer was separated, dried (Na$_2$SO$_4$) and evaporated to yield title product as a foam, 3.0 g; pnmr/CDCl$_3$/TMS 1.40 (3H, s), 1.55 (3H, s), 3.70 (3H, m), 4.31 (1H, s), 4.58 (1H, m), 5.04 (2H, s), 7.24 (5H, s).

The aqueous layer was concentrated to yield crystalline 6-alpha-(aminomethyl)penicillanic acid 1,1-dioxide, 3.1 g, having pnmr fully identical with the same completely hydrogenated product of Example 8.

Method B

Title product of Example 8 (3.0 g, 11.45 moles) was dissolved in 100 ml 1:1 H$_2$O:methanol. The pH was adjusted and maintained at 8.3–8.7 as benzyl chloroformate (1.79 g, 12.59 mole) was added dropwise over several minutes. Following a brief period of stirring the pH was adjusted to 6.0 with 1 N HCl and THF removed by distillation in vacuo. The aqueous residue was extracted with 30 ml of ethyl acetate and the extract discarded. Fresh ethyl acetate (50 ml) was added and the pH adjusted to 1.8 with 1 N HCl. The aqueous layer was extracted with 50 ml fresh ethyl acetate. The combined organic layer and extract was washed 1×50 ml saturated NaCl, dried (Na$_2$SO$_4$) and evaporated in vacuo to yield title product as a foam, 3.7 g, having pnmr identical with that of title product obtained according to Method A immediately above.

The title products of Examples 7, 30, 32, 39 and 41 are converted to the corresponding N-benzyloxycarbonyl derivatives by use of the same acylation procedure.

EXAMPLE 17

Pivaloyloxymethyl 6-alpha-(Benzyloxycarbonylaminomethyl)penicillanate 1,1-Dioxide The title product of the preceding Example 6.75 g, 17 mmoles) and N,N-diisopropylethylamine (3.34 ml, 18.7 mmoles) were dissolved in dimethylformamide (50 ml), chloromethyl pivalate (2.72 ml, 18.7 mmoles) were added, and the mixture allowed to stir at ambient temperature for 20 hours. The reaction mixture was diluted with ethyl ether (300 ml), washed with water (2×100 ml), dried ($Na_2SO_4$) and evaporated in vacuo to an oil. The oil was dissolved in 100 ml ether, washed 3×50 ml $H_2O$, dried ($Na_2SO_4$) and concentrated in vacuo to yield purified title product as a viscous oil, 4.4 g, pnmr/$CDCl_3$/TMS 1.20 (9H, s), 1.34 (3H, s), 1.51 (3H, s), 3.64 (3H, m), 4.31 (1H, s), 4.60 (1H, d), 5.04 (2H, s), 5.71 (2H, g), 7.24 (5H, s).

The same method, but substituting an equivalent amount of bromomethyl acetate or 1-ethoxycarbonyloxyethyl chloride, as appropriate, is used to prepare the corresponding acetoxymethyl and 1-ethoxycarbonyloxyethyl 6-alpha-(benzyloxycarbonylaminomethyl)penicillanate 1,1-dioxides.

By the same methods the 6-beta-(benzyloxycarbonylaminomethyl) and 6-(1-benzyloxycarbonylaminoethyl)acids of the preceding Example are converted to corresponding esters.

EXAMPLE 18 p-Toluenesulfonate Salt of Pivaloyloxymethyl 6-alpha-(Aminomethyl)penicillanate 1,1-Dioxide Title product of the preceding Example (1.8 g, 3.53 mmoles) was hydrogenated in a mixture of THF (40 ml) and $H_2O$ (20 ml) over 1.8 g of 10% Pd/C in the presence of pyridinium p-toluenesulfonate (1.77 g, 7.06 mmoles) at 50 psig for 1.5 hours. The catalyst was recovered by filtration over diatomaceous earth and the filtrate stripped of THF in vacuo, during which the title product crystallized, 1.2 g, mp 214°–215° C. (dec.); pnmr/DMSO-$d_6$/TMS 1.16 (9H, s), 1.32 (3H, s), 1.48 (3H, s), 2.28 (3H, s), 3.34 (2H, m), 3.82 (1H, m), 4.60 (1H, s), 5.14 (1H, d, J=2 Hz), 5.75 (2H, ABq), 7.23 (4H, ABq).

Anal. Calcd. for $C_{15}H_{24}O_7N_2S \cdot C_7H_7SO_3H$: C, 48.16; H, 5.88; N, 5.11. Found: C, 48.31; H, 6.11; N, 5.08.

By the same method, other benzyloxycarbonyl derivatives of the preceding Example are converted to the corresponding pivaloyloxymethyl and acetoxymethyl esters of 6-alpha(aminomethyl)-, 6-beta-(aminomethyl)-, 6-alpha-(1-aminoethyl)-, and 6-beta-(1-aminoethyl)-penicillanic acid 1,1-dioxides.

EXAMPLE 19

Chloromethyl 6-alpha-(Benzyloxycarbonylaminomethyl)penicillanate 1,1-Dioxide

Title product of Example 16 (1 g) is combined with 10 ml of methylene chloride and 2 ml of water and the pH adjusted to 8.0 with 40% tetrabutylammonium hydroxide over a period of 15 minutes. The methylene chloride layer is separated and the aqueous layer extracted with three 2 ml portions of fresh methylene chloride. The methylene chloride layers are combined, dried over $Na_2SO_4$, and concentrated in vacuo to yield tetrabutylammonium salt. The salt is combined with 10 ml of chloroiodomethane, the mixture stirred for 16 hours, and concentrated to dryness in vacuo to yield present title product.

By the same method, the corresponding 6-beta epimer of Example 16 is converted to its chloromethyl ester.

EXAMPLE 20

Iodomethyl 6-alpha-(Benzyloxycarbonylaminomethyl)penicillanate, 1,1-Dioxide

Title product of the preceding Example (0.24 g) is combined with 3 ml of acetone and sodium iodide (0.58 g) and the mixture stirred for 16 hours. The reaction mixture is concentrated in vacuo and the residue distributed between 7.5 ml of ethyl acetate and 5.0 ml of water. The ethyl acetate is separated, washed in sequence with two 25 ml portions of water and one 25 ml portion of brine, dried over $Na_2SO_4$ and concentrated in vacuo to provide present title product.

By the same method, the other chloromethyl ester of the preceding Example is converted to its iodomethyl ester.

EXAMPLE 21

6-beta-(D-2-Azido-2-phenylacetamido)penicillanoyloxymethyl 6'-alpha-Benzyloxycarbonylaminomethyl)penicillanate 1',1'-Dioxide A mixture of 3.5 g of 6-beta-(D-2-azido-2-phenylacetamido)penicillanic acid (azidocillin) sodium salt in 20 ml of methylene chloride and 20 ml of water was treated with sufficient 6 N hydrochloric acid to give a pH of 2.0. Tetrabutylammonium hydroxide (40% in water) was gradually added until the pH was 7.0. The organic phase was separated and the aqueous layer further extracted (2×20 ml) with fresh methylene chloride. The methylene chloride layers were combined, dried over sodium sulfate and concentrated under vacuum to give 4.2 g of the corresponding tetrabutylammonium salt.

The tetrabutylammonium salt (1.65 g, 2.7 mmoles) and the title iodomethyl ester of the preceding Example (2.7 mmoles) are combined in 20 ml of acetone and stirred to dissolve. After 15 minutes, the reaction mixture is concentrated in vacuo to yield title product.

By the same method, the other iodomethyl ester of the preceding Example is converted to the corresponding bis-methanediol ester with 6-beta-(D-2-azido-2-phenylacetamido)penicillanic acid.

By the same method, both iodomethyl esters of the preceding Example are reacted with the tetrabutylammonium salts of compounds of the formula

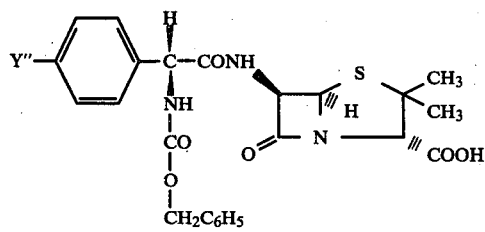

wherein Y" is hydrogen, benzyloxycarbonyloxy, acetoxy, isopropionyloxy, adipoyloxy, isovaleroyloxy, ethoxycarbonyloxy, isobutyroyloxy, benzoyloxy, o-chlorobenzoyloxy, m-bromobenzoyloxy, p-fluorobenzoyloxy, m-ethylbenzoyloxy or p-methoxybenzoyloxy to yield the corresponding methanediol bis-esters with 6'-alpha and 6'-beta-(benzyloxycarbonylaminomethyl)-penicillanic acid 1,1-dioxide.

EXAMPLE 22

6-beta-(D-2-Amino-2-phenylacetamido)penicillanoyloxymethyl 6'-alpha-(Aminomethyl)penicillanate 1',1'-Dioxide Title compound of the preceding Example (1.4 g) is combined with 30 ml of methylene chloride and 30 ml of isopropyl alcohol and hydrogenated at 50 psi over 2.0 g of 10% Pd/C until substantially 2 equivalents of $H_2$ are taken up. An additional portion (1.5 g) of catalyst is added if hydrogenation stops prematurely and hydrogenation continued. The catalyst is recovered by filtration with 1:1 methylene chloride:isopropyl alcohol wash. The combined filtrate and wash are concentrated in vacuo to yield title product.

By the same method the corresponding 6'-beta-analog is converted to 6-beta-(D-2-amino-2-phenylacetamidol)penicillanoyloxymethyl 6'-beta-(aminomethyl)penicillanate 1',1'-dioxide.

Also by the same method the N-benzyloxycarbonyl containing bis-esters of the preceding Example are converted to the corresponding 6'-alpha- and 6'-beta-aminomethyl derivatives. In the case of the O-benzyloxycarbonyl intermediates, 3 equivalents of hydrogen are utilized to produce the amoxicillin analogs.

EXAMPLE 23

Benzyl 6-alpha-(Benzyloxycarbonylaminomethyl)penicillanate and Benzyl 6-beta-(Benzyloxycarbonylaminomethyl)penicillanate The required Grignard agent was prepared essentially according to the method of DiNinno et al., J. Org. Chem. 42, pp. 2960-2965 (1977). Thus benzyl 6-alpha-iodopenicillanate was dissolved in 75 ml of dry tetrahydrofuran and cooled to −78° C. under dry $N_2$. Methylmagnesium bromide (5.6 ml of 3 M in ether) was added dropwise. After stirring an additional 15 minutes, a solution of benzyloxycarbonylaminomethyl acetate (1.87 g) in 25 ml of dry tetrahydrofuran was added in one portion. After a second 15 minutes of stirring at −78° C., acetic acid (2 ml) was added, the mixture warmed to 0° C. and evaporated in vacuo. The residue was distributed between 250 ml ethyl acetate and 50 ml of water. The organic layer was separated, washed 1×100 ml saturated $NaHCO_3$ and 2×100 ml brine, dried over $Na_2SO_4$, and evaporated in vacuo to an oil (7.3 g). The oil was chromatographed on 250 g silica gel, eluting with 1:10 ethyl acetate:chloroform in 20 ml fractions. Fractions 20-24 contained 1.3 g of a side product (oil); fractions 25-34 contained 0.62 g of a 3:2 beta:alpha mixture of title products by pnmr assay. Fractions 35-60 contained 2.2 g of a 3:1 alpha:beta mixture of title products.

If desired the title epimers are separated by repeat chromatography of combined fractions 25-60 on 350 g of silica gel, using the same eluant.

Alternatively, fractions 25-60 are combined, then following the procedures of Examples 3-6, oxidized and equilibrated at C.6 to yield pure title product of Example 6.

EXAMPLE 24

Benzyl 6-alpha-Bromo-6-beta-(1R-trifluoromethanesulfonyloxyethyl)penicillanate

Benzyl 6-alpha-bromo-6-beta-(1R-hydroxyethyl)-penicillanate (DiNinno et al., J. Org. Chem. 42, pp. 2960-2965, 1977; 20.28 g, 0.0489 mole) was dissolved in 400 ml $CH_2Cl_2$ and chilled with an acetone-ice bath. Pyridine (7.91 ml, 2 equivalents) was added and then, dropwise, trifluoromethanesulfonic anhydride (11.58 ml, 1.4 equivalents) maintaining temperature ±5°. The mixture was stirred at 0° for 30 minutes, diluted with $CH_2Cl_2$, washed sequentially with saturated $NaHCO_3$, $H_2O$ and saturated NaCl, evaporated in vacuo, and diluted with 1:1 hexane, thereby crystallizing title product, 18.71 g; pnmr/$CDCl_3$/delta/TMS: 1.42 (3H, s), 1.55 (3H, d, J=6 Hz), 1.66 (3H, s), 4.58 (1H, s), 5.20 (2H, s), 5.34 (1H, q, J=6 Hz), 5.56 (1H, s), 7.38 (5H, s).

EXAMPLE 25

Benzyl 6-alpha-Bromo-6-beta-(1S-azidoethyl)penicillanate

Title product of the preceding Example (34.4 g, 0.0628 mole) was dissolved in 400 ml of $CH_2Cl_2$. Tetrabutylammonium azide (25.0 g, 1.4 equivalents) in 100 ml $CH_2Cl_2$ was added dropwise and the mixture stirred for one hour at 25° C. The $CH_2Cl_2$ was stripped in vacuo and the residual oil filtered through 500 g of silica gel on a sintered glass funnel, eluting with 2 liters $CH_2Cl_2$. Evaporation gave title product as a pale yellow oil, 27 g; pnmr/$CDCl_3$/delta/TMS: 1.40 (3H, s), 1.53 (3H, d, J=6.3 Hz), 1.57 (3H, s), 4.10 (1H, q, J=6.3 Hz), 4.47 (1H, s), 5.19 (2H, s), 5.61 (1H, s), 7.34 (5H, s).

EXAMPLE 26

Benzyl 6-beta-(1S-Aminoethyl)-6-alpha-bromopenicillanate

Title product of the preceding Example (27.0 g, 0.0613 mole) was dissolved in 300 ml $CHCl_3$. Triethylamine (35 ml, 4 equivalents) was added and then $H_2S$ was bubbled through the reaction mixture for 3.5 hours. The reaction mixture was then flushed with $N_2$ for 0.5 hour and stripped of $CHCl_3$ in vacuo. The resulting oil was distributed between ether and 1 N HCl (200 ml). The ether layer was extracted 3×200 ml fresh 1 N HCl. The combined aqueous layers were diluted with ethyl acetate and the pH of the two phase system adjusted to 8.5. The organic layer was separated and evaporated to yield title product as an oil (6.34 g). The original ether layer was diluted with water and the pH adjusted to 8.5. The ether layer was separated and evaporated to yield additional title product, 6.0 g, pnmr/$CDCl_3$/delta/TMS: 1.28 (3H, d, J=6.3 Hz), 1.40 (3H, s), 1.58 (3H, s), 3.34 (1H, q, J=6.3 Hz), 4.45 (1H, s), 5.16 (2H, s), 5.54 (1H, s), 7.33 (5H, s).

EXAMPLE 27

Benzyl 6-beta-(1S-Benzyloxycarbonylaminoethyl)-6-alpha-bromo-penicillanate

Benzyl chloroformate (5.10 ml, 1.2 equivalents) was dissolved in 20 ml of $CH_2Cl_2$, chilled in an acetone-ice bath. A solution of title product of the preceding Example (12.34 g, 0.02980 mole) in 50 ml of $CH_2Cl_2$ containing diisopropylethylamine (7.78 ml, 1.5 equivalents) was added dropwise, maintaining the temperature 0°–5° C. with an ice water bath. The reaction mixture was stirred for 20 minutes, stripped of $CH_2Cl_2$ in vacuo, diluted with ethyl acetate and water (pH was noted to be 8.2), and adjusted to pH 2.0 with dilute HCl. The organic layer was separated, washed with $H_2O$ and then saturated NaCl and evaporated to yield title product as a pale yellow oil, 17 g; pnmr/$CDCl_3$/delta/TMS: 1.35 (3H, s), 1.38 (3H, d), 1.55 (3H, s), 4.26 (1H, m), 4.45 (1H, s), 4.97 (1H, d), 5.08 (2H, S), 5.14 (2H, s), 5.53 (1H, s), 7.33 (10H, s).

EXAMPLE 28

Benzyl 6-beta-(1S-Benzyloxycarbonylaminoethyl)penicillanate

Title product of the preceding Example (16.33 g, 0.0298 mole) was dissolved in 200 ml benzene. Tri-n-butyltin hydride (23.5 ml, 3 equivalents) was added and the mixture refluxed 3 hours. Benzene was removed in vacuo and title product crystallized from the residue by addition of hexane, 9.26 g; pnmr/$CDCl_3$/delta/TMS: 1.39 (3H, d, J=6 Hz), 1.40 (3H, s), 1.63 (3H, s), 3.62 (1H, dd, J=4, 11 Hz), 4.12 (1H, m), 4.39 (1H, s), 4.81 (1H, d, J=8 Hz), 5.08 (2H, s), 5.17 (2H, s), 5.32 (1H, d, J=4 Hz), 7.32 (5H, s), 7.36 (5H, s).

EXAMPLE 29

Benzyl 6-beta-(1S-Benzyloxycarbonylaminoethyl)penicillanate 1,1-Dioxide

By the procedure of Example 5, title product of the preceding Example (4.0 g, 0.0085 mole) was converted to present title product, isolated as a white foam, 4.25 g; pnmr/$CDCl_3$/delta/TMS: 1.21 (3H, s), 1.33 (3H, d, J=6 Hz), 1.48 (3H, s), 4.20 (1H, m), 4.35 (1H, m), 4.40 (1H, s), 4.53 (1H, d, J=4.5 Hz), 5.08 (2H, s), 5.17 (2H, q), 5.45 (1H, d, J=7 Hz), 7.30 (5H, s), 7.35 (5H, s).

EXAMPLE 30

6-beta-(1S-Aminoethyl)penicillanic Acid 1,1-Dioxide

Using 180 mg of 5% Pd/C as catalyst, title product of the preceding Example (175 mg) was converted to present title product by the procedure of Example 7. After recovery of the catalyst, the combined mother liquor and tetrahydrofuran/$H_2O$ washes were stripped of the former in vacuo and title product recovered by freeze drying the aqueous residue overnight, ir (KBr): 1765 $cm^{-1}$; pnmr/$D_2O$/delta/DSS: 1.47 (3H, s), 1.53 (3H, d), 1.60 (3H, s), 4.35 (2H, m), 4.37 (1H, s), 5.12 (1H, d, J=4 Hz).

EXAMPLE 31

Benzyl 6-alpha-(1S-Benzyloxycarbonylaminoethyl)penicillanate 1,1-Dioxide

Title product of Example 29 (4.25 g, 0.0085 mole) was dissolved in 100 ml $CH_2Cl_2$. DBN (0.96 ml, 1 equivalent) was added dropwise and the mixture stirred three minutes at 25°, then quenched by adding to 1 ml (2 equivalents) of glacial $CH_3CO_2H$. The quenched mixture was diluted with $CH_2Cl_2$, washed in sequence with dilute HCl (pH 2.5), water and saturated NaCl, and evaporated in vacuo to yield crude title product as a white foam, 4.5 g. Column chromatography on silica gel, using 9:1 $CH_2Cl_2$:ethyl acetate as eluant, gave purified title product, white foam, 2.83 g, pnmr/$CDCl_3$/delta/TMS: 1.21 (3H, s), 1.35 (3H, d, J=7 Hz), 1.51 (3H, s), 3.78 (1H, dd, J=2, 4 Hz), 4.27 (1H, m), 4.36 (1H, s), 4.56 (1H, d, J=2 Hz), 5.09 (2H, s), 5.16 (2H, q), 7.3 (10H, s).

EXAMPLE 32

6-alpha-(1S-Aminoethyl)penicillanic Acid 1,1-Dioxide

5% Pd/C (4.5 g) was slurried in 50 ml $H_2O$ and prehydrogenated for 1.5 hours at 25°/50 psig. Title product of the previous Example (2.83 g) was dissolved in 50 ml ethyl acetate, added to the prehydrogenated aqueous catalyst slurry, and hydrogenated at 25°/50 psig for 0.5 hour. Catalyst was recovered by filtration. The aqueous layer was separated. Title product crystallized in three crops (1.1 g total weight) as the aqueous layer was concentrated; pnmr/$D_2O$/delta/DDS: 1.47 (3H, s), 1.52 (3H, d), 1.62 (3H, s), 4.05 (2H, m), 4.28 (1H, s), 5.10 (1H, d); ir (KBr) 1787 $cm^{-1}$.

EXAMPLE 33

Benzyl 6-beta-Bromo-6-alpha-(1-trifluoromethylsulfonyloxyethyl)penicillanate By the procedure of Example 24, benzyl 6-beta-bromo-6-alpha-(1-hydroxymethyl)penicillanate (a mixture of side chain epimers; DiNinno et al., loc cit.; 8.90 g, 0.0214 mole) was converted to present title products. On addition of 1:1 hexane:ether a first crop of solids crystallized (4.70 g) which was primarily the 1R side chain epimer. (If desired, this epimer is carried through the procedures of Examples 25–30 to yield the title product of Example 32). The second crop of solids (2.40 g) and the third crop (an oil, 1.60 g) were mixed side chain epimers of title product, primarily the 1S side chain epimer; pnmr/$CDCl_3$/delta/TMS: 1.41 (3H, s), 1.65 (3H, s), 1.78 (3H, d, J=6.5 Hz), 4.56 (1H, s), 5.22 (2H, s), 5.37 (1H, q, J=6.5 Hz), 5.48 (1H, s), 7.4 (5H, s).

EXAMPLE 34

Benzyl 6-alpha-(1-Azidoethyl)-6-beta-bromopenicillanate

Second and third crops (primarily 1S side-chain epimer) of title product of the preceding Example (4.0 g, 0.0073 mole) were converted to present title product (primarily 1R side chain epimer) by the procedure of Example 25. This product was isolated as a pale yellow oil, 2.91 g, pnmr/$CDCl_3$/delta/TMS: 1.40 (3H, s), 1.56 (3H, d, J=6.5 Hz), 4.00 (1H, q, J=6.5 Hz), 4.48 (1H, s), 5.16 (2H, s), 5.34 (1H, s), 7.32 (5H, s).

EXAMPLE 35

Benzyl 6-alpha-(1R-Aminoethyl)-6-beta-bromopenicillanate and

Benzyl 6-alpha-(1S-Aminoethyl)-6-beta-bromopenicillanate

Title product of the previous Example (primarily the 1R side chain epimer; 2.91 g, 0.0066 mole) was converted to present title products according to the procedure of Example 26. Following removal of CHCl$_3$ used as reaction solvent, the residue was distributed between ether and 1 N HCl (200 ml). The ether layer was separated and extracted 1×200 ml 1 N HCl. The combined aqueous layers were layered with ethyl acetate and the pH adjusted to 8.5. The aqueous layer was separated and extracted with fresh ethyl acetate. The ethyl acetate layers were combined and evaporated to yield a mixture of title products (primarily the 1R isomer) as an oil, 1.53 g. The isomers were separated by column chromatography on 200 g silica gel, eluting with 1:1 CH$_2$Cl$_2$:ethyl acetate, monitoring by tlc (3:2 CH$_2$Cl$_2$:ethyl acetate). Clean, faster moving fractions (R$_f$0.52) were combined and evaporated to yield title 1S isomer (0.172 g), which, if desired, is converted by the procedures of Examples 27-30 to title product of Example 32. Middle cuts gave a mixture of title products (0.45 g), which, if desired, is rechromatographed to yield additional pure products. Clean, slower moving fractions (R$_f$ 0.47) were combined to yield title 1R side-chain epimer, 0.674 g, pnmr/CDCl$_3$/delta/TMS: 1.29 (3H, d, J=6 Hz), 1.38 (3H, s), 1.64 (3H, s), 3.29 (1H, q, J=6 Hz), 4.51 (1H, s), 5.17 (2H, s), 5.38 (1H, s), 7.33 (5H, s).

EXAMPLE 36

Benzyl 6-beta-Bromo-6-alpha-(1R-benzyloxycarbonylaminoethyl)penicillanate

By the procedure of Example 27, 1R side chain title product of the preceding Example (0.674 g, 0.0016 mole) was converted to present title product, 0.877 g, R$_f$0.85 (1:1 CH$_2$Cl$_2$:ethyl acetate).

EXAMPLE 37

Benzyl 6-beta-(1R-Benzyloxycarbonylaminoethyl)penicillanate

By the procedure of Example 28, title product of the preceding Example (0.877 g, 0.0016 mole) was converted to present title product. After stripping, the benzene used as solvent, the residue was triturated 4×50 ml with hexane to yield crude product as an oil (627 mg). The oil was chromatographed on silica gel eluting with 19:1 chloroform:ethyl acetate to yield purified title product, 569 mg, pnmr/CDCl$_3$/delta/TMS: 1.10 (3H, d, J=6.5 Hz), 1.36 (3H, s), 1.60 (3H, s), 3.41 (1H, dd, J=4, 11 Hz), 4.16 (1H, m), 4.43 (1H, s), 5.08 (2H, s), 5.13 (2H, s), 5.32 (1H, d, J=4 Hz), 7.29 (5H, s), 7.33 (5H, s).

EXAMPLE 38

Benzyl 6-beta-(1R-Benzyloxycarbonylaminoethyl)penicillanate 1,1-Dioxide

By the procedure of Example 5, title product of the preceding Example (0.569 g, 0.0012 mole) was converted to present title product, 0.681 g, pnmr/CDCl$_3$/delta/TMS: 1.22 (3H, s), 1.27 (3H, d), 1.47 (3H, s), 3.94 (1H, dd, J=4, 12 Hz), 4.42 (1H, s), 4.48 (2H, m), 5.04 (2H, s), 5.13 (2H, q), 5.40 (1H, d, J=8), 7.27 (5H, s), 7.32 (5H, s).

EXAMPLE 39

6-beta-(1R-Aminoethyl)penicillanic Acid 1,1-Dioxide

Using 400 mg of 5% Pd/C, title product of the preceding Example (202 mg) was converted to present title product, 50 mg; ir (KBr) 1788 cm$^{-1}$; pnmr/D$_2$O/delta/DDS: 1.45 (3H, s), 1.51 (3H, d), 1.57 (3H, s), 4.27 (1H, m), 4.33 (1H, s), 4.85 (1H, m), 5.15 (1H, d, J=4 Hz).

EXAMPLE 40

Benzyl 6-alpha-(1R-Benzyloxycarbonylaminoethyl)penicillanate 1,1-Dioxide

By the procedure of Example 31, using 19:1 CHCl$_3$:ethyl acetate as eluant in the chromatography, title product of Example 38 (368 mg) was converted to present title product, 285 mg; pnmr/CDCl$_3$/delta/TMS: 1.23 (3H, s), 1.33 (3H, d, J=6.5 Hz), 1.50 (3H, s), 3.61 (1H, dd, J=2, 9 Hz), 4.28 (1H, m), 4.34 (1H, s), 4.67 (1H, d, J=2 Hz), 4.98 (1H, d), 5.07 (2H, s), 5.18 (2H, q), 7.30 (5H, s), 7.35 (5H, s).

EXAMPLE 41

6-alpha-(1R-Aminoethyl)penicillanic Acid 1,1-Dioxide

By the procedure of Example 39, title product of the preceding Example (285 mg) was converted to present title product (132 mg; ir (KBr) 1768 cm$^{-1}$; pnmr/D$_2$O/delta/DDS: 1.47 (3H, s), 1.54 (3H, d), 1.61 (3H, s), 4.03 (2H, m), 4.44 (1H, s), 5.10 (1H, d, J=2).

EXAMPLE 42

Capsule

The following materials are blended to obtain a powder of uniform composition in the proportions by weight indicated below:

| | |
|---|---|
| (a) Pivaloyloxymethyl 6-alpha(aminomethyl)penicillanate 1,1-dioxide p-toluenesulfonate | 1.0 |
| (b) Ampicillin trihydrate | 1.0 |
| (c) Lactose | 0.5 |
| (d) Polyethylene glycol, average molecular weight, 4000 | 3.0 |

Blend (1375 mg) is filled into suitably sized hard gelatin capsules to obtain capsules of 250 mg potency of each active ingredient. Higher or lower potency capsules are prepared by appropriate adjustment of capsule size and fill weight. The relative weights of active ingredients are adjusted to obtain capsules wherein the weight ratio of active ingredients is other than one, e.g., the ingredients are blended in a weight ratio of 0.75, 1.5, 0.5 and 3.0, respectively, with a 1700 mg fill weight/capsule to obtain capsules having 225 mg potency of (a) and 450 mg potency of (b).

In like manner, the other beta-lactamase inhibitors of the present invention are formulated with other conventional beta-lactam antibiotics for oral use.

EXAMPLE 43

Injectable Preparation

Sterile cefoperazone sodium and 6-beta(aminomethyl)penicillanic acid 1,1-dioxide (500 mg of each) are weighed into 15 ml vials, under sterile conditions. The vials are vacuum sealed with rubber plugs. Prior to injection, sterile water for injection (10 ml) is introduced through the rubber plug and the vial shaken to dissolve. Solution (1–10 ml) is removed via hypodermic needle through the rubber plug and injected intramuscularly.

For i.v. infusion, a larger container is employed and the antibiotic combination is made up to a dilution of 2.5–10 mg/ml with isotonic solution and slowly infused intravenously.

EXAMPLE 44

Chloromethyl 6-[D-(2-Azido-2-phenylacetamido)]penicillanate

A solution of 12.0 g (0.03 mole) 6-[D-(2-azido-2-phenylacetamido)]penicillanic acid sodium salt, 25 ml water was combined with 100 ml methylene chloride and 10.17 g (0.03 mole) tetrabutylammonium hydrogen sulfate. The mixture (pH 3.0) was adjusted to pH 7.5 with sodium bicarbonate, the organic layer is separated and the aqueous layer was extracted with 2×100 ml methylene chloride. The combined organic layers were dried ($Na_2SO_4$) and the solvent evaporated to yield a solid residue. The residue was triturated with ethyl acetate (300 ml), filtered, the cake washed with ethyl acetate followed by ethyl ether and dried under nitrogen to afford 16.5 g (89%) of tetrabutylammonium salt.

A mixture of 12.32 g (0.02 mole) of the above salt was combined with 70 ml chloroiodomethane and the mixture stirred overnight at ambient temperature. The reaction mixture was concentrated to dryness and the residue purified by chromatography on 600 g silica gel, eluting with 1:1 ethyl acetate/hexane by volume to afford 8.1 g (95%) of the desired chloromethyl ester as a pale yellow viscous oil, pnmr/$CDCl_3$: 1.58 (s, 3H), 1.68 (s, 3H), 4.45 (s, 1H), 5.1 (s, 1H), 5.5–5.9 (dd m, 4H), 7.2 (d, 1H) and 7.4 (s, 5H) ppm.

Chloromethyl 6-[2-azido-2-(p-acetoxyphenyl)acetamido]penicillanate is obtained in like manner.

EXAMPLE 45

Iodomethyl 6-[D-(2-Azido-2-phenylacetamido)]penicillanate

Title product of the preceding Example (1.45 g, 0.00342 mole) in 30 ml acetone was purged 3 minutes with $N_2$. NaI (2.55 g, 0.01714 mole) was added and the resulting solution stirred 16 hours at ambient temperature. The reaction mixture was clarified by filtration, the filtrate concentrated in vacuo, and the residue taken into 75 ml $CHCl_3$ and filtered. The $CHCl_3$ filtrate was washed 2×30 ml saturated NaCl, dried ($Na_2SO_4$) and concentrated to yield title product as a foam, 1.23 g, pnmr/$CDCl_3$/TMS/delta (ppm): 1.53 (3H, s), 1.64 (3H, s), 4.37 (1H, s), 5.05 (1H, s), 5.56 (2H, m, J=4, 11 Hz), 5.87 (2H, ABq), 7.31 (5H, s).

Iodomethyl 6-[2-azido-2-(p-acetoxyphenyl)acetamido]penicillanate is obtained in like manner.

EXAMPLE 46

6-alpha-(Benzyloxycarbonylaminomethyl)-1,1-dioxopenicillanoyloxymethyl 6-[D-(2-Azido-2-phenylacetamido)]penicillanate Title product of Example 16 (0.56 g, 1.43 mmoles) was dissolved in 50 ml $CH_2Cl_2$. $H_2O$ (20 ml) was added and the pH adjusted to 8.6 with 1 N NaOH. $NaHCO_3$ (0.121 g, 1.43 mmoles) was added followed by tetrabutylammonium hydrogen sulfate (0.488 g, 1.43 mmoles) in portions, while maintaining pH 8.0–8.3 with 1 N NaOH, until near the end of the addition, when the pH was allowed to drop to 7.0. After stirring the mixture 15 minutes, the layers were separated. The aqueous layer was extracted 1×30 ml fresh $CH_2Cl_2$. The combined organic layer and extract was dried ($Na_2SO_4$) and concentrated in vacuo to yield tetrabutylammonium 6-alpha-(benzyloxycarbonylaminomethyl)penicillanate 1,1-dioxide as a foam. The latter was dissolved in 20 ml acetone and added to a solution of title product of the preceding Example (0.714 g, 1.43 mmoles) in 15 ml acetone and the mixture stirred 1 hour at ambient temperature, concentrated in vacuo and the residue slurried in 30 ml of ethyl acetate to yield crystalline tetrabutylammonium iodide (0.42 g). The filtrate was evaporated to a foam (1.2 g) which was chromatographed on 100 g silica gel eluting with 20% ethyl acetate/$CHCl_3$ in 20 ml fractions. Clean product fractions ($R_f$ 0.22 on tlc with the same eluant) were combined and concentrated in vacuo to yield purified title product as a foam, 0.61 g, pnmr/$CDCl_3$/delta (ppm): 1.33 (3H, s), 1.48 (3H, s), 1.52 (3H, s), 1.59 (3H, s), 3.65 (3H, m), 4.33 (1H, s), 4.42 (1H, s), 4.61 (1H, s [br]), 5.05 (3H, s), 5.58 (5H, m), 7.24 (5H, s), 7.32 (5H, s).

By appropriate substitution of reagents, 6-alpha-(benzyloxycarbonylaminomethyl)-1,1-dioxopenicillanoyloxymethyl 6-[2-azido-2-(p-acetoxyphenyl)acetamido]penicillanate; 6-beta-(benzyloxycarbonylaminomethyl)-1,1-dioxopenicillanoyloxymethyl 6-[D-(2-azido-2-phenylacetamido)]penicillanate; and 6-beta-[1S-(benzyloxycarbonylamino)ethyl]-1,1-dioxopenicillanoyloxymethyl 6-[D-(2-azido-2-phenylacetamido)]penicillanate are prepared in like manner.

EXAMPLE 47

Di(p-toluenesulfonate) Salt of 6-alpha-(Aminomethyl)-1,1-dioxopenicillanoyloxymethyl 6-[D-2-Amino-2-phenylacetamido]penicillanate Pd/C (10%, 2 g) was prehydrogenated in 20 ml of water. A solution of title product of the preceding Example (0.96 g, 1.226 mmoles) in 30 ml THF and then pyridinium p-toluenesulfonate (0.615 g, 2.452 mmoles) were added, and the mixture hydrogenated for 1.5 hours at 50 psig. Catalyst was recovered by filtration over diatomaceous earth with THF and $H_2O$ wash. THF was removed from the combined filtrate and washes by concentration in vacuo. The aqueous residue was extracted 3×30 ml ethyl acetate and freeze dried to yield title product, 0.66 g, contaminated with unreduced benzyloxycarbonyl compound. Fresh 10% Pd/C (1.0 g) was prehydrogenated in 20 ml of $H_2O$. The contaminated title product (0.5 g) was dissolved in 30 ml THF and then added to the prereduced catalyst slurry. Finally, fresh pyridinium p-toluenesulfonate (0.315 g) was added and the mixture hydrogenated at 50 psig for 1.5 hours. Catalyst was recovered and purified title product recovered as above, 0.5 g, pnmr/DMSO-d$_6$/TMS/delta (250 MHz): 1.35 (6H, br. s), 1.47 (6H, s), 2.30 (6H, s), 3.38 (2H, m), 3.94 (1H, m), 4.45 (1H, s), 4.72 (1H, s), 5.08 (1H, br. s), 5.31 (1H, br. s), 5.45 (1H, d, J=4 Hz), 5.60 (1H, m), 5.93 (2H, m), 7.32 (8H, ABq), 7.48 (5H, m).

By the same method, the other compounds of the preceding Example are reduced to 6-alpha-(aminomethyl)-1,1-dioxopenicillanoyloxymethyl 6-[2-amino-2-(p-acetoxyphenyl)acetamido]penicillanate; 6-beta-(aminomethyl)-1,1-dioxopenicillanoyloxymethyl 6-[D-(2-amino-2-phenylacetamido)]penicillanate; and 6-beta-(1S-aminoethyl)-1,1-dioxopenicillanoyloxymethyl 6-[D-(2-amino-2-phenylacetamido)]penicillanate.

EXAMPLE 48

1,1-Dioxopenicillanoyloxymethyl 6-alpha-(Benzyloxycarbonylaminomethyl)penicillanate 1,1-Dioxide Title product of Example 16 (0.5 g, 1.26 mmoles) was dissolved in 50 ml CH$_2$Cl$_2$.H$_2$O (10 ml) was added and the pH adjusted to 8.6 with 1 N NaOH. NaHCO$_3$ (0.106 g, 1.26 mmoles) and then tetrabutylammonium hydrogen sulfate (0.428 g, 1.26 mmoles) were added. The pH, which dropped to 5.0, was adjusted to 7.5 with 1 N NaOH. After stirring 30 minutes at ambient temperature, the organic layer was separated, dried (Na$_2$SO$_4$) and concentrated in vacuo to yield tetrabutylammonium 6-alpha-(benzyloxycarbonylaminomethyl)-penicillanate 1,1-dioxide as a foam. The latter was dissolved in 20 ml of acetone. Iodomethyl penicillanate 1,1-dioxide (prepared, for example, according to Godtfredsen et al., U.S. Pat. No. 4,342,772; 0.47 g) in 15 ml acetone was added and the mixture stirred for 5 minutes, and then concentrated in vacuo. The residue was slurried in 30 ml of ethyl acetate and crystalline tetrabutylammonium iodide (0.33 g) recovered by filtration. The filtrate was concentrated in vacuo. The residue was slurried in 30 ml of ethyl acetate and crystalline tetrabutylammonium iodide (0.33 g) recovered by filtration. The filtrate was concentrated in vacuo to yield title product as a foam, 0.82 g, pnmr/CDCl$_3$/TMS/delta (ppm): 1.40 (3H, s), 1.42 (3H, s), 1.58 (6H, s), 3.41 (2H, m), 3.69 (3H, m), 4.40 (2H, s), 4.58 (2H, m), 5.08 (2H, s), 5.59 (1H, m), 5.86 (2H, s), 7.29 (5H, s).

1,1-Dioxopenicillanoyloxymethyl 6-beta-(benzyloxycarbonylaminomethyl)penicillanate 1,1-dioxide; and 1,1-dioxopenicillanoyloxymethyl 6-alpha-(1S-benzyloxycarbonylaminoethyl)penicillanate 1,1-dioxide are prepared in like manner.

EXAMPLE 49 p-Toluenesulfonate Salt of 1,1-Dioxopenicillanoyloxymethyl 6-alpha-(Aminomethyl)penicillanate 1,1-Dioxide Pd/C (10%, 1.2 g) was prehydrogenated in 10 ml H$_2$O. Pyridinium tosylate (0.482 g, 1.92 mmoles) and then a solution of title product of the preceding Example in 30 ml THF were added and the mixture hydrogenated at 50 psig for 1 hour. Catalyst was recovered by filtration over diatomaceous earth, with THF/H$_2$O wash. THF was removed from the combined filtrate and wash by concentration in vacuo. The aqueous residue was extracted 1×30 ml ethyl acetate. The organic layer was dried (Na$_2$SO$_4$) and concentrated to yield 60 mg of solids. The aqueous layer was concentrated to 10 ml. Crystalline title product was recovered by filtration, 100 mg; mp 228°–229° C. (dec); pnmr/DMSO-d$_6$/delta (250 MHz): 1.35 (3H, s), 1.37 (3H, s), 1.49 (3H, s), 1.50 (3H, s), 2.29 (3H, s), 3.29 (1H, dd, J=1.7, 16.6 Hz), 3.39 (2H, m), 3.72 (1H, dd, J=4.6, 16.6 Hz), 3.92 (1H, m), 4.60 (1H, s), 4.77 (1H, s), 5.21 (2H, m), 5.96 (2H, s), 7.31 (4H, ABq).

Anal. Calcd. for C$_{18}$H$_{25}$N$_3$O$_{10}$S$_2$.CH$_3$C$_6$H$_4$SO$_3$H: C, 44.17; H, 4.89; N, 6.18. Found: C, 45.53; H, 4.76; N, 6.10.

The aqueous mother liquor was freeze dried to yield 160 mg solids. These were slurried in a small amount of water, filtered, washed with a small amount of ethyl acetate and dried to yield an additional 70 mg of purified title product, having identical mp and pnmr.

1,1-Dioxopenicillanoyloxymethyl 6-beta-(aminomethyl)penicillanate 1,1-dioxide; and 1,1-dioxopenicillanoyloxymethyl 6-alpha-(1S-aminoethyl)penicillanate 1,1-dioxide are prepared in like manner.

EXAMPLE 50

Chloromethyl 6-alpha-(Benzyloxycarbonylaminomethyl)penicillanate 1,1-Dioxide

By the method of Example 46, title product of Example 16 (0.396 g, 1.0 mmole) was converted to its tetrabutylammonium salt. The latter was dissolved in 30 ml bromochloromethane, stirred at ambient temperature for 18 hours, concentrated in vacuo to a foam, and chromatographed on 50 g silica gel with 20% ethyl acetate/CHCl$_3$ as eluant in 20 ml fractions. Fractions 6–10 were combined and concentrated in vacuo to a foam, 0.25 g, R$_f$ 0.7 on tlc with same eluant; pnmr/CDCl$_3$/TMS/delta (ppm): 1.37 (3H, s), 1.54 (3H, s), 3.70 (3H, m), 4.38 (1H, s), 4.67 (1H, br s), 5.07 (2H, s), 5.66 (1H, d, J=9 Hz), 5.70 (2H, ABq), 7.33 (5H, s).

Chloromethyl 6-alpha-(1R-benzyloxycarbonylaminoethyl)penicillanate 1,1-dioxide and chloromethyl-6-beta-(1R-benzyloxycarbonylaminoethyl)penicillanate 1,1-dioxide are prepared in like manner.

EXAMPLE 51

Iodomethyl 6-alpha-(Benzyloxycarbonylaminomethyl)penicillanate 1,1-Dioxide

Title product of the preceding Example (0.25 g, 0.563 mmole) was dissolved in 15 ml of acetone and purged with N$_2$. NaI (0.42 g, 2.8 mmoles) was added and the resulting solution stirred 17 hours and then concentrated in vacuo. The solids were triturated with CHCl$_3$, insolubles removed by filtration and title product recovered from filtrate by concentration in vacuo to a foam, 0.23 g, pnmr/CDCl$_3$/TMS/delta (ppm): 1.39 (3H, s), 1.55 (3H, s), 3.64 (3H, m), 4.28 (1H, s), 4.59 (1H, br. s), 5.04 (2H, s), 5.48 (1H, m), 5.83 (2H, ABq), 5.23 (5H, s).

In like manner, the other chloromethyl esters of the preceding Example are converted to corresponding iodomethyl esters.

EXAMPLE 52

Methylene bis-[6-alpha-(Benzyloxycarbonylaminomethyl)-1,1-dioxopenicillanate]

Title product of Example 16 (0.17 g, 0.429 mmole) was converted to its tetrabutylammonium salt (0.27 g) according to the procedure of Example 46. The latter was dissolved in 10 ml acetone and added to a solution of title product of the preceding Example (0.23 g, 0.429 mmole) in 10 ml acetone. The mixture was stirred 15 minutes, concentrated to a foam in vacuo and the foam slurried in 20 ml ethyl acetate. The slurry was filtered to yield tetrabutylammonium iodide (110 mg) and the filtrate concentrated in vacuo to yield title product as a foam, 0.28 g, pnmr/CDCl$_3$/TMS/delta (ppm): 1.36 (6H, s), 1.52 (6H, s), 3.73 (6H, m), 4.40 (2H, s), 4.69 (2H, br. s), 5.08 (4H, s), 5.77 (4H, m), 7.28 (10H, s).

By the same method, the other iodomethyl esters are reacted with their corresponding salts to obtain methylene bis-[6-alpha-(1R-benzyloxycarbonylaminoethyl)-1,1-dioxopenicillanate] and methylene bis-[6-beta-(1R-benzyloxycarbonylaminoethyl)-1,1-dioxopenicillanate].

EXAMPLE 53 bis-(p-Toluenesulfonate) Salt of Methylene bis-[6-alpha-(Aminomethyl)-1,1-dioxopenicillanate]

By the procedure of Example 49, title product of the preceding Example was hydrogenated. After recovery of catalyst and removal of THF, the aqueous residue was extracted 3×20 ml ethyl acetate and freeze dried to yield title product, 0.19 g, pnmr/DMSO-d$_6$/TMS/delta (250 MHz): 1.37 (6H, s), 1.50 (6H, s), 2.31 (6H, s), 3.40 (4H, m), 3.94 (2H, m), 4.77 (2H, s), 5.30 (2H, m), 5.98 (2H, m), 7.32 (8H, ABq).

By the same method, the other bis-esters of the preceding Example are converted to bis-(p-toluenesulfonate) salts of methylene bis-[6-alpha-(1R-aminoethyl)-1,1-dioxopenicillanate] and methylene bis-[6-beta-(1R-aminoethyl)-1,1-dioxopenicillanate].

I claim:

1. A compound having the stereochemical formula

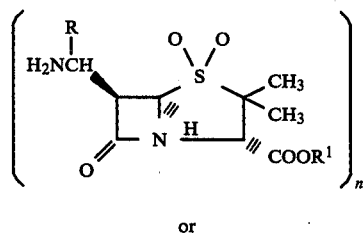

(I)

or

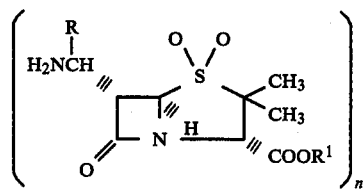

(II)

wherein
R is hydrogen or methyl; and
n is 1 and R$^1$ is hydrogen, a radical group forming an ester hydrolyzable under physiological conditions, or 1,1-dioxopenicillanoyloxymethyl; or
n is 2 and R$^1$ is —CH$_2$—;
a pharmaceutically-acceptable acid addition salt thereof or a pharmaceutically-acceptable cationic salt thereof when R$^1$ is hydrogen.

2. A compound of claim 1 wherein n is 1 and R$^1$ is: gamma-butyrolacton-4-yl,
—CHR$^2$OCOR$^3$, or
—CHR$^2$OCOOR$^3$, wherein R$^2$ is hydrogen or methyl and R$^3$ is (C$_1$–C$_6$)alkyl.

3. A compound of claim 2 wherein R$^1$ is 1-ethoxycarbonyloxyethyl.

4. A compound of claim 2 wherein R$^1$ is pivaloyloxymethyl.

5. A compound of claim 4 wherein R is hydrogen.

6. The compound of claim 5 having the formula (II).

7. The compound of claim 6 which is in the form of its p-toluenesulfonic acid addition salt.

8. A compound of claim 1 wherein n is 1 and R$^1$ is hydrogen.

9. A compound of claim 8 having the stereochemical formula (I).

10. A compound of claim 8 having the stereochemical formula (II).

11. A compound of claim 8 wherein R is hydrogen.

12. A compound of claim 8 wherein R is methyl.

13. A compound of claim 8 wherein the aminoalkyl side chain is 1S-aminoethyl.

14. A compound of claim 8 wherein the aminoalkyl side chain is 1R-aminoethyl.

15. A compound of claim 1 wherein n is 1 and R$^1$ is 1,1-dioxopenicillanoyloxymethyl.

16. A compound of claim 15 wherein R is hydrogen.

17. The compound of claim 16 having the formula (II).

18. A compound of claim 1 wherein n is 2 and R$^1$ is —CH$_2$—.

19. A compound of claim 18 wherein R is hydrogen.

20. The compound of claim 19 having the formula (II).

21. A pharmaceutical composition for treating bacterial infections which comprises an antibacterially effective amount of a compound of claim 1 and a beta-lactam antibiotic in a weight ratio of 1:3 to 3:1.

22. A pharmaceutical composition of claim 21 wherein the beta-lactam antibiotic is
amoxicillin,
ampicillin,
azlocillin,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefmenoxime
cefonicid
cefodizime
cefoperazone,
ceforanide,
cefotaxime,
cefoxitin,
cefsulodin,
ceftazidime,
ceftizoxime,
ceftriaxone,
cefuroxime,
cephacetrile,
cephalexin,
cephaloglycin, cephaloridine,
cephalothin,
cephapirin,
cephradine,
cyclacillin,
epicillin,
hetacillin,
levopropylcillin,
mecillinam,
mezlocillin,
penicillin G,
penicillin V,
phenethicillin,
piperacillin,
pirbenicillin,
pivampicillin,
sarmoxicillin,
sarpicillin,
suncillin,
talampicillin or
ticarcillin; or
a pharmaceutically acceptable salt thereof.

23. A pharmaceutical composition of claim 22 wherein n is 1 and $R^1$ is hydrogen.

24. A pharmaceutical composition of claim 22 wherein n is 1 and $R^1$ is:
gamma-butyrolacton-4-yl,
—$CHR^2OCOR^3$, or
—$CHR^2OCOOR^3$,
wherein $R^2$ is hydrogen or methyl and $R^3$ is ($C_1$-$C_6$)alkyl.

25. A pharmaceutical composition of claim 24 wherein $R^1$ is pivaloyloxymethyl.

26. A pharmaceutical composition of claim 22 wherein n is 1 and $R^1$ is 1,1-dioxopenicillanoyloxymethyl.

27. A pharmaceutical composition of claim 22 wherein n is 2 and $R^1$ is —$CH_2$—.

28. A pharmaceutical composition of claim 22 wherein R is hydrogen.

29. A pharmaceutical composition of claim 22 wherein R is methyl.

30. A pharmaceutical composition of claim 22 wherein the beta-lactam antibiotic is ampicillin, hetacillin, pivampicillin, bacampicillin or talampicillin.

31. A pharmaceutical composition of claim 22 wherein the beta-lactam antibiotic is amoxicillin, sarmoxicillin or sarpicillin.

32. A pharmaceutical composition of claim 22 wherein the beta-lactam antibiotic is cefoperazone.

33. A method of treating a bacterial infection in a mammal which comprises administering to said mammal an antibacterially effective amount of a pharmaceutical composition of claim 22.

34. A method of treating a bacterial infection in a mammal which comprises administering to said mammal an antibacterially effective amount of a pharmaceutical composition of claim 23.

35. A method of treating a bacterial infection in a mammal which comprises administering to said mammal an antibacterially effective amount of a pharmaceutical composition of claim 24.

36. A method of treating a bacterial infection in a mammal which comprises administering to said mammal an antibacterially effective amount of a pharmaceutical composition of claim 25.

37. A method of treating a bacterial infection in a mammal which comprises administering to said mammal an antibacterially effective amount of a pharmaceutical composition of claim 36.

38. A method of treating a bacterial infection in a mammal which comprises administering to said mammal an antibacterially effective amount of a pharmaceutical composition of claim 27.

39. A method of treating a bacterial infection in a mammal which comprises administering to said mammal an antibacterially effective amount of a pharmaceutical composition of claim 28.

40. A method of treaing a bacterial infection in a mammal which comprises administering to said mammal an antibacterially effective amount of a pharmaceutical composition of claim 29.

41. A compound having the stereochemical formula

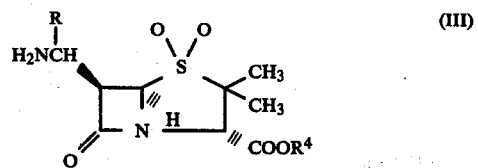

(III)

or

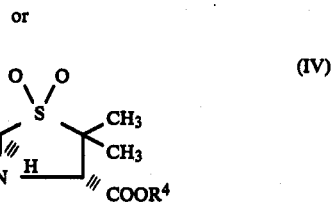

(IV)

wherein R is hydrogen or methyl and $R^4$ is

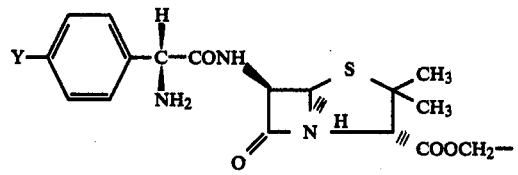

wherein Y is hydrogen,
hydroxy,
($C_2$-$C_7$)-alkanoyloxy,
($C_2$-$C_7$)-alkoxycarbonyloxy,
benzoyloxy, or
benzoyloxy monosubstituted
with ($C_1$-$C_4$)-alkyl, ($C_1$-$C_4$)-alkoxy or halo.

42. A compound of claim 41 wherein Y is hydrogen.

43. A compound of claim 41 wherein Y is hydroxy.

44. A compound of claim 42 wherein R is hydrogen.

45. A compound of claim 42 wherein R is methyl.

46. A pharmaceutical composition suitable for treating a bacterial infection in a mammal which comprises an antibacterially effective amount of a compound of claim 41.

47. A method of treating a bacterial infection in a mammal which comprises administering to said mammal an antibacterially effective amount of a pharmaceutical composition of claim 46.

48. A compound of the stereochemical formula

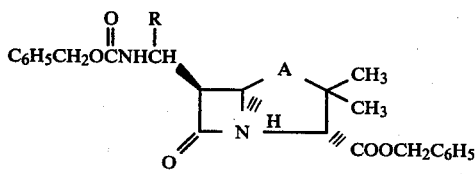

or

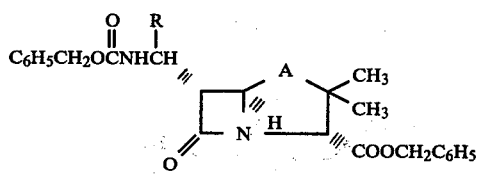

wherein R is hydrogen or methyl, and A is

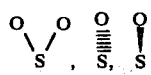

or S.

49. A compound of the stereochemical formula

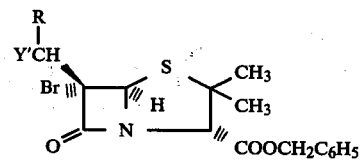

or

-continued

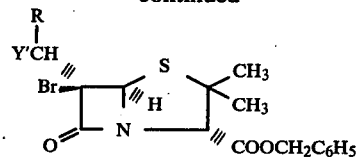

wherein R is hydrogen or methyl and Y' is benzyloxycarbonylamino,
amino,
azido, or
trifluoromethanesulfonyloxy.

50. A compound having the stereochemical formula

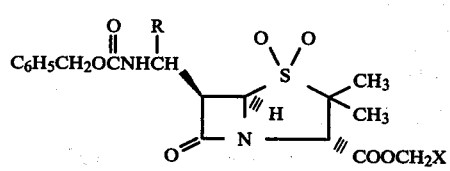

or

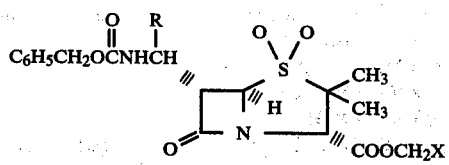

wherein R is hydrogen or methyl and X is chloro or iodo.

51. The compound of claim 10 wherein R is hydrogen.

52. A pharmaceutical composition of claim 23 wherein the compound has the formula (II) and R is hydrogen.

53. A pharmaceutical composition of claim 25 wherein the compound has the formula (II) and R is hydrogen.

54. A method of treating a bacterial infection in a mammal which comprises administering to said mammal an antibacterially effective amount of a pharmaceutical composition of claim 52.

55. A method of treating a bacterial infection in a mammal which comprises administering to said mammal an antibacterially effective amount of a pharmaceutical composition of claim 53.

* * * * *